United States Patent
Laugel et al.

(10) Patent No.: US 10,689,620 B2
(45) Date of Patent: Jun. 23, 2020

(54) T CELLS WITH INCREASED IMMUNOSUPPRESSION RESISTANCE

(71) Applicant: Adaptimmune Limited, Abingdon, Oxfordshire (GB)

(72) Inventors: Bruno Laugel, Abingdon (GB); Kathrin Skibbe, Abingdon (GB)

(73) Assignee: ADAPTIMMUNE LIMITED, Abingdon, Oxfordshire (GB)

( * ) Notice: Subject to any disclaimer, the term of this patent is extended or adjusted under 35 U.S.C. 154(b) by 264 days.

(21) Appl. No.: 15/949,018

(22) Filed: Apr. 9, 2018

(65) Prior Publication Data

US 2018/0298338 A1    Oct. 18, 2018

Related U.S. Application Data

(62) Division of application No. 15/713,464, filed on Sep. 22, 2017, now Pat. No. 9,976,121.

(30) Foreign Application Priority Data

Sep. 23, 2016 (GB) .................................. 1616238.0

(51) Int. Cl.
| | |
|---|---|
| C12N 5/0783 | (2010.01) |
| C12N 9/16 | (2006.01) |
| A61K 39/00 | (2006.01) |
| A61K 35/17 | (2015.01) |
| C07K 14/725 | (2006.01) |
| C12N 15/86 | (2006.01) |

(52) U.S. Cl.
CPC ............ *C12N 5/0638* (2013.01); *A61K 35/17* (2013.01); *A61K 39/0011* (2013.01); *C07K 14/7051* (2013.01); *C12N 5/0636* (2013.01); *C12N 9/16* (2013.01); *C12N 15/86* (2013.01); *C12Y 301/04053* (2013.01); *A61K 2039/5156* (2013.01); *A61K 2039/5158* (2013.01); *C12N 2501/01* (2013.01); *C12N 2510/00* (2013.01); *C12N 2740/15043* (2013.01)

(58) Field of Classification Search
CPC ................................................ C12N 5/0638
See application file for complete search history.

(56) References Cited

U.S. PATENT DOCUMENTS 9,976,121 B2    5/2018 Laugel et al.

FOREIGN PATENT DOCUMENTS

WO    1993/019767 A1    10/1993

OTHER PUBLICATIONS

Bjørgo et al. (Crit Rev Immunol. 2006; 26(5):443-51) (Year: 2006).*
Abrahamsen et al.; "TCR- and CD28-Mediated Recruitment of Phosphodiesterase 4 to Lipid Rafts Potentiates TCR Signaling," The Journal of Immunology, (2004) 173:pp. 4847-4858.
Bacher et al.; "Interferon-α Suppresses cAMP to Disarm Human Regulatory T Cells," Cancer Research; 73(18), Sep. 15, 2013 (published online Jul. 22, 2013); pp. 5647-5656.
Han et al.; "PDE7A1, a cAMP-specific Phosphodiesterase, Inhibits cAMP-dependent Protein Kinase by a Direct Interaction with C*;" The Journal of Biological Chemistry, vol. 281, No. 22; Jun. 2, 2006; pp. 15050-15057; doi: 10.1074/jbc.M601333200.
International Search Report and Written Opinion dated Dec. 15, 2017 for International Application No. PCT/EP2017/074139, titled: T Cells With Increased Immunosuppression Resistance.
Kalinski; "Regulation of Immune Responses by Prostaglandin E2;" J. Immunol., Jan. 1, 2012, 188(1): 21-28; pp. 1-18; doi:10.4049/jimmunol.1101029.
Kress, et al., "Elevated Cyclic AMP Levels in T Lymphocytes Transformed by Human T-Cell Lymphotrpoic Virus Type 1," Journal of Virology, vol. 84; No. 17; pp. 8732-8742 (2010).
Notice of Allowance for U.S. Appl. No. 15/713,464, dated Apr. 2, 2018.
Office Action for U.S. Appl. No. 15/713,464, dated Nov. 22, 2017.
Ohta; "A Metabolic Immune Checkpoint: Adenosine in Tumor Microenvironment;" Frontiers in Immunology, Mar. 29, 2016, vol. 7, Article 109; pp. 1-11; doi: 10.3389/fimmu.2016.00109.
Wu et al.; "Over-expressing Akt in T cells to resist tumor immunosuppression and increase anti-tumor activity," BMC Cancer, (2015); vol. 15, No. 603, pp. 1-10.

* cited by examiner

*Primary Examiner* — Scott Long
(74) *Attorney, Agent, or Firm* — Hamilton, Brook, Smith & Reynolds, P.C.

(57) ABSTRACT

This invention relates to the treatment of cancer in an individual by administration of a population of modified T cells that express a recombinant cAMP phosphodiesterase (PDE) or a fragment thereof and an antigen receptor which binds specifically to cancer cells in the individual. Populations of modified T cells and methods of producing populations of modified T cells are provided, along with pharmaceutical compositions and methods of treatment.

17 Claims, 11 Drawing Sheets
(2 of 11 Drawing Sheet(s) Filed in Color)
Specification includes a Sequence Listing.

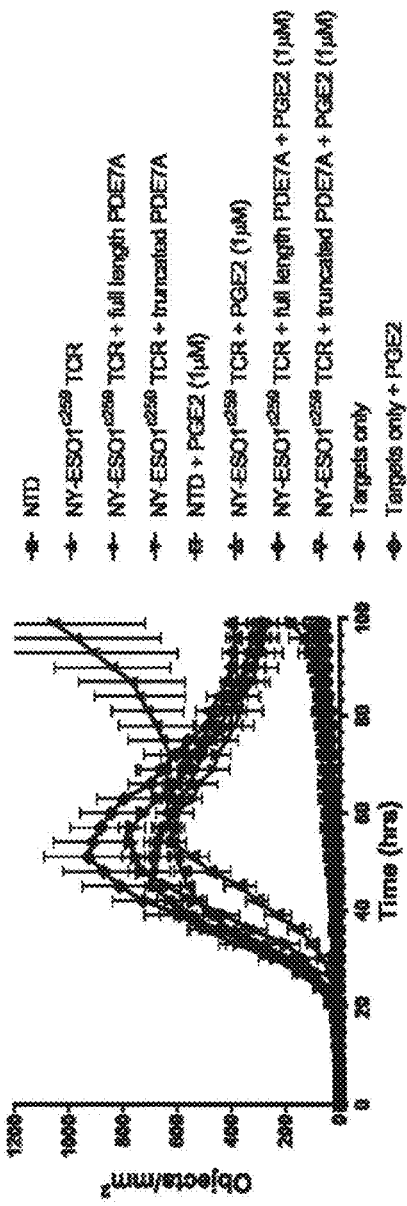
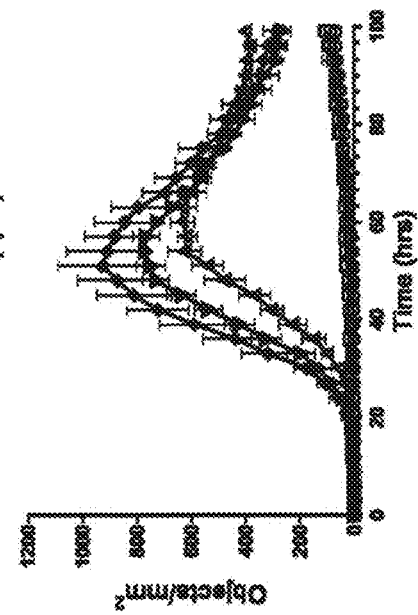
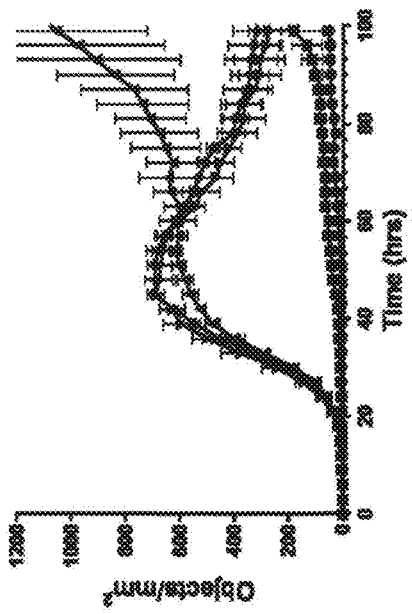
FIG. 9A
FIG. 9B
FIG. 9C

T CELLS WITH INCREASED IMMUNOSUPPRESSION RESISTANCE

RELATED APPLICATIONS

This application is a divisional of U.S. patent application Ser. No. 15/713,464, filed Sep. 22, 2017, now U.S. Pat. No. 9,976,121, issued May 22, 2018, which claims priority under 35 U.S.C. § 119 or 365 to GB Application No. 1616238.0, filed Sep. 23, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 54981000002_seqlist.txt; created Jun. 5, 2018, 46 KB in size.

FIELD

The present invention relates to the modification of T cells to increase their resistance to immunosuppression and the use of modified T cells in immunotherapy, for example for the treatment of cancer.

BACKGROUND

T cells (or T lymphocytes) are found widely distributed within tissues and the tumour environment. T cells are distinguished from other lymphocytes by the presence of T cell receptors (TCRs) on the cell surface. The TCR is a multi-subunit transmembrane complex that mediates the antigen-specific activation of T cells. The TCR confers antigen specificity on the T cell, by recognising an antigen peptide ligand that is presented on the target cell by a major histocompatibility complex (MHC) molecule.

Although peptides derived from altered or mutated proteins in tumour target cells can be recognised as foreign by T cells expressing specific TCRs, many antigens on tumour cells are simply upregulated or overexpressed (so called self-antigens) and do not induce a functional T cell response. Therefore, studies have focussed on identifying target tumour antigens which are expressed, or highly expressed, in the malignant but not the normal cell type. Examples of such targets include the cancer/testis (CT) antigen NY-ESO-1, which is expressed in a wide array of human cancers but shows restricted expression in normal tissues (Chen Y-T et al. Proc Natl Acad Sci USA. 1997; 94(5):1914-1918), and the MAGE-A family of CT antigens which are expressed in a very limited number of healthy tissues (Scanlan M. J. et al. Immunol Rev. 2002; 188:22-32).

Identification of such antigens has promoted the development of targeted T cell-based immunotherapy, which has the potential to provide specific and effective cancer therapy (Ho, W. Y. et al. Cancer Cell 2003; 3:1318-1328; Morris, E. C. et al. Clin. Exp. Immunol. 2003; 131:1-7; Rosenberg, S. A. Nature 2001; 411:380-384; Boon, T. and van der Bruggen P. J. Exp. Med. 1996; 183:725-729).

However, the microenvironment of a tumour is often immunosuppressive and prevents the successful immunotherapy of cancer (Rabinovich G. A. et al. Annu Rev Immunol. 2007; 25:267-296). Extracellular adenosine is a known inhibitor of immune function. High levels of adenosine in tumours have been found to play a significant role in the evasion of anti-tumour immune responses (Blay J. et al. Cancer Res. 1997; 57:2602-2605; Ohta A. et al. Proc Natl Acad Sci USA. 2006; 103:13132-13137). The adenosine-rich environment in tumours may induce T cell anergy (Zarek P. E. et al. Blood 2008; 111:251-259; Ohta A. et al. J Immunol. 2009; 183:5487-5493), increase production of immunosuppressive cytokines (e.g., TGF-beta, IL-10) (Zarek P. E. et al. supra; Nowak M. et al. Eur J Immunol. 2010; 40:682-687), and discourage cellular immune responses by targeting antigen-presenting cells (Hasko G. et al. Faseb J. 2000; 1 4:2065-2074; Panther E. et al. Blood 2003; 101: 3985-3990).

Prostaglandin E2 (PGE2) is also known to be an inhibitor of immune functions and has been widely demonstrated to suppress both innate and antigen-specific immunity (Phipps R. P. et al. Immunol Today. 1991; 12:349-352; Harris S. G. et al. Trends Immunol. 2002; 23:144-150).

T cell-based immunotherapies which are more able to cope with the hostile tumour environment would be useful in providing more effective cancer therapy.

SUMMARY

The present inventors have recognised that the cytotoxicity of T cells targeting tumour cells may be increased by the inhibition of cAMP signalling for example through recombinant expression of a cAMP phosphodiesterase (PDE) or fragment thereof. T cells modified to express a cAMP PDE or fragment thereof may therefore be useful in cancer immunotherapy.

An aspect of the invention provides a method of treating cancer in an individual comprising;

administering to the individual a population of T cells that express a recombinant cAMP phosphodiesterase (PDE) or a fragment thereof and an antigen receptor which binds specifically to cancer cells in the individual.

Another aspect of the invention provides a method of producing a population of modified T cells comprising;

providing a population of T cells obtained from an individual, and modifying the T cells to express a cAMP phosphodiesterase (PDE) or a fragment thereof, thereby producing a population of modified T cells.

In some embodiments, the T cells may express an endogenous antigen receptor, such as a T cell receptor (TCR), which binds specifically to cancer cells from the individual. In other embodiments, a method may further comprise modifying the T cells to express an antigen receptor which binds specifically to cancer cells from the individual. The T cells may be modified to express the antigen receptor before, after or at the same time as they are modified to express the cAMP PDE or fragment.

Following modification, the population of modified T cells may be expanded, stored and/or formulated into a pharmaceutical composition.

Another aspect of the invention provides a method of treating cancer in an individual comprising;

providing a population of T cells obtained from a donor individual, modifying the T cells to express a cAMP phosphodiesterase (PDE) or a fragment thereof, thereby producing a population of modified T cells, and administering the population of modified T cells to a recipient individual.

In some embodiments, the T cells may express an endogenous antigen receptor which binds specifically to cancer cells from the donor individual. In other embodiments, a method may further comprise modifying the T cells to express an antigen receptor which binds specifically to cancer cells from the donor individual. The T cells may be modified to express the antigen receptor before, after or at the same time as they are modified to express the cAMP PDE or fragment.

The donor individual and the recipient individual may be the same (i.e. autologous treatment; the modified T cells are obtained from an individual who is subsequently treated with the modified T cells) or the donor individual and the recipient individual may be different (i.e. allogeneic treatment; the modified T cells are obtained from one individual and subsequently used to treat a different individual).

Another aspect of the invention provides a population of modified T cells which express an antigen receptor which binds specifically to cancer cells and a cAMP phosphodiesterase (PDE) or fragment thereof, wherein said cells comprise a heterologous nucleic acid encoding the cAMP phosphodiesterase (PDE) or fragment thereof.

The antigen receptor may be endogenous or may be a recombinant antigen receptor encoded by heterologous nucleic acid.

Other aspects of the invention provide pharmaceutical compositions comprising the modified T cells described above, methods of treatment comprising administering the modified T cells or pharmaceutical compositions to an individual and modified T cells or pharmaceutical compositions for use in a method of treatment, for example, a method of treatment of cancer in an individual.

Other aspects of the invention provide nucleic acid comprising a nucleotide sequence encoding an antigen receptor which binds specifically to cancer cells and a nucleotide sequence encoding a cAMP phosphodiesterase (PDE) or fragment thereof, vectors comprising the nucleic acid, including lentiviral vectors, and methods of making viral particles comprising the vectors.

BRIEF DESCRIPTION OF FIGURES

The patent or application file contains at least one drawing executed in color. Copies of this patent or patent application publication with color drawings will be provided by the Office upon request and payment of the necessary fee.

FIG. 2A and FIG. 2B (data from two donors) show that NY-ESO specific T cells overexpressing PDE7A have increased ability to induce apoptosis in A375 melanoma target cells compared to NY-ESO specific T cells alone.

FIG. 3A and FIG. 3B (data from two donors) show that NY-ESO specific T cells overexpressing PDE7A are resistant to the T cell-inhibitory effects of PGE2, demonstrating A375 melanoma target cell killing ability that is comparable to that shown by the same T cells in the absence of PGE2.

FIG. 4A and FIG. 4B (data from two donors) show that NY-ESO specific T cells overexpressing PDE7A demonstrate superior killing ability in the presence of forskolin than NY-ESO specific T cells that do not overexpress PDE7A (ADB869 T cells).

FIG. 6A and FIG. 6B (data from two donors) show that overexpression of PDE4C in NY-ESO specific T cells partially blocks the inhibitory effects of PGE2 and forskolin on IFN-γ secretion.

FIG. 9A shows target cell killing kinetics by NY-ESO specific T cells that overexpress full-length or truncated PDE7A in the presence and absence of PGE2. FIG. 9B shows comparable killing ability for all constructs in the absence of inhibitors. FIG. 9C shows that NY-ESO specific T cells overexpressing full-length or truncated PDE7A demonstrate superior killing ability in the presence of PGE2 than NY-ESO specific T cells that do not overexpress PDE7A.

FIG. 10A and FIG. 10B (data from two donors) show that overexpression of full-length or truncated PDE7A in NY-ESO specific T cells partially blocks the inhibitory effects of PGE2 and forskolin on IFN-γ secretion.

DETAILED DESCRIPTION

Figure 1A:
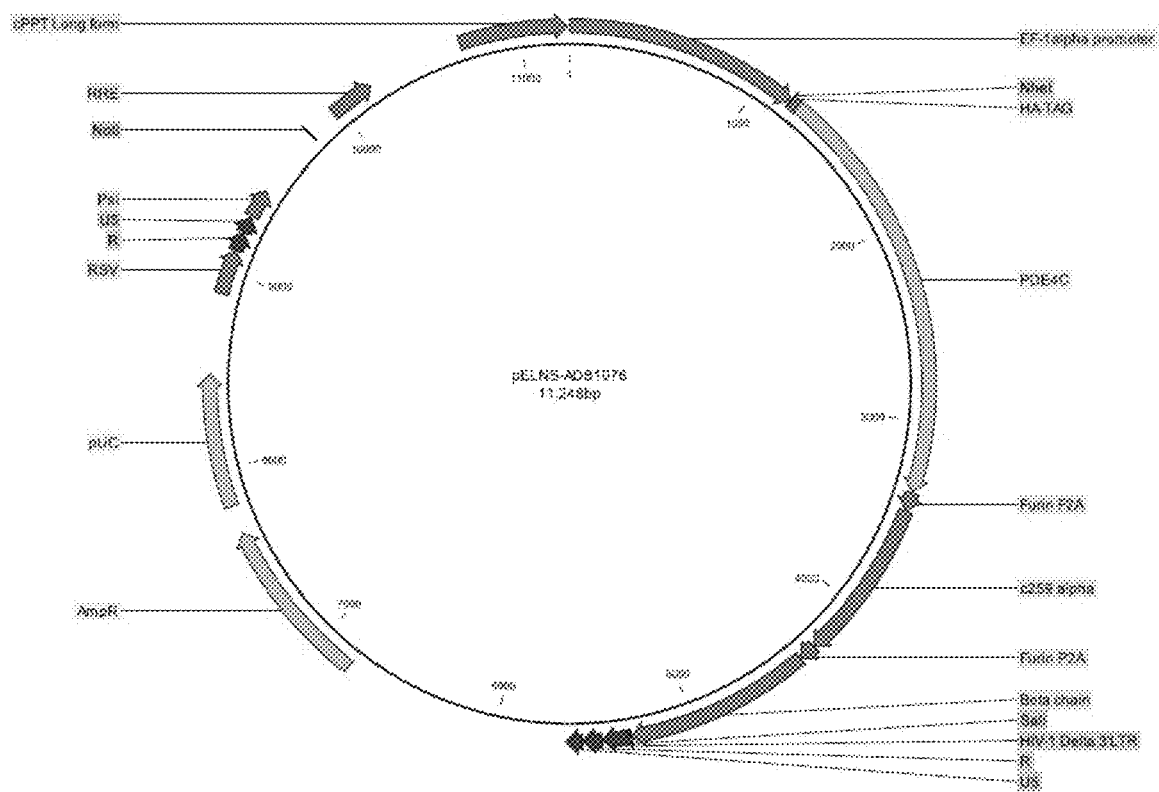
FIGS. 1A and 1B show plasmid maps of lentivectors expressing the NY-ESO$^{c259}$ T cell receptor in tandem with PDE4C (FIG. 1A) or PDE7A (FIG. 1B).

This invention relates to methods of increasing the resistance of anti-tumour T cells to the immunosuppressive microenvironment of tumours through recombinant expression of a cAMP PDE or a fragment of a cAMP PDE. Reducing cAMP signalling through expression of a cAMP PDE or fragment thereof is shown herein to increase the resistance of anti-tumour T cells to inhibition by adenosine and prostaglandin E2 (PGE2). Modified T cells with increased resistance to inhibition may display increased cytotoxicity and/or cytokine release relative to unmodified T cells. Anti-tumour T cells modified to express cAMP PDE or a cAMP PDE fragment as described herein may be useful in immunotherapy, for example adoptive cell transfer (ACT) for the treatment of cancer.

T cells (also called T lymphocytes) are white blood cells that play a central role in cell-mediated immunity. T cells can be distinguished from other lymphocytes by the presence of a T cell receptor (TCR) on the cell surface. There are several types of T cells, each type having a distinct function.

T helper cells (T$_H$ cells) are known as CD4$^+$ T cells because they express the CD4 surface glycoprotein. CD4$^+$ T cells play an important role in the adaptive immune system and help the activity of other immune cells by releasing T cell cytokines and helping to suppress or regulate immune responses. They are essential for the activation and growth of cytotoxic T cells.

Cytotoxic T cells (Tc cells, CTLs, killer T cells) are known as CD8+ T cells because they express the CD8 surface glycoprotein. CD8+ T cells act to destroy virus-infected cells and tumour cells. Most CD8+ T cells express TCRs that can recognise a specific antigen displayed on the surface of infected or damaged cells by a class I MHC molecule. Specific binding of the TCR and CD8 glycoprotein to the antigen and MHC molecule leads to T cell-mediated destruction of the infected or damaged cells.

T cells for use as described herein may be CD4+ T cells; CD8+ T cells; or CD4+ T cells and CD8+ T cells. For example, the T cells may be a mixed population of CD4+ T cells and CD8+ T cells.

Suitable T cells for use as described herein may be obtained from a donor individual. In some embodiments, the donor individual may be the same person as the recipient individual to whom the T cells will be administered following modification and expansion as described herein (autologous treatment). In other embodiments, the donor individual may be a different person to the recipient individual to whom the T cells will be administered following modification and expansion as described herein (allogeneic treatment). For example, the donor individual may be a healthy individual who is human leukocyte antigen (HLA) matched (either before or after donation) with a recipient individual suffering from cancer.

A method described herein may comprise the step of obtaining T cells from an individual and/or isolating T cells from a sample obtained from an individual with cancer.

A population of T cells may be isolated from a blood sample. Suitable methods for the isolation of T cells are well known in the art and include, for example fluorescent activated cell sorting (FACS: see for example, Rheinherz et al (1979) PNAS 76 4061), cell panning (see for example, Lum et al (1982) Cell Immunol 72 122) and isolation using antibody coated magnetic beads (see, for example, Gaudernack et al 1986 J Immunol Methods 90 179). CD4+ and CD8+ T cells may be isolated from the population of peripheral blood mononuclear cells (PBMCs) obtained from a blood sample. PBMCs may be extracted from a blood sample using standard techniques. For example, ficoll may be used in combination with gradient centrifugation (Böyum A. Scand J Clin Lab Invest. 1968; 21(Suppl.97):77-89), to separate whole blood into a top layer of plasma, followed by a layer of PBMCs and a bottom fraction of polymorphonuclear cells and erythrocytes. In some embodiments, the PBMCs may be depleted of CD14+ cells (monocytes).

Following isolation, the T cells may be activated. Suitable methods for activating T cells are well known in the art. For example, the isolated T cells may be exposed to a T cell receptor (TCR) agonist. Suitable TCR agonists include ligands, such as a peptide displayed on a class I or II MHC molecule on the surface of an antigen presenting cell, such as a dendritic cell, and soluble factors, such as anti-TCR antibodies.

An anti-TCR antibody may specifically bind to a component of the TCR, such as εCD3, αCD3 or αCD28. Anti-TCR antibodies suitable for TCR stimulation are well-known in the art (e.g. OKT3) and available from commercial suppliers (e.g. eBioscience CO USA). In some embodiments, T cells may be activated by exposure to anti-αCD3 antibodies and IL2. More preferably, T cells are activated by exposure to anti-αCD3 antibodies and anti-αCD28 antibodies. The activation may occur in the presence or absence of CD14+ monocytes. Preferably, the T cells may be activated with anti-CD3 and anti-CD28 antibody coated beads. For example, PBMCs or T cell subsets including CD4+ and/or CD8+ cells may be activated, without feeder cells (antigen presenting cells) or antigen, using antibody coated beads, for example magnetic beads coated with anti-CD3 and anti-CD28 antibodies, such as Dynabeads® Human T-Activator CD3/CD28 (ThermoFisher Scientific).

Following isolation and activation, the T cells may be modified to express cyclic adenosine monophosphate (cAMP) phosphodiesterase (PDE) or a fragment of a cAMP PDE.

The cAMP PDE or fragment inhibits cAMP signalling in a cell by hydrolysing phosphodiester bonds and catalysing the decomposition of adenosine 3',5'-cyclic phosphate (cyclic adenosine monophosphate; cAMP) to adenosine 5'-phosphate (adenosine monophosphate; AMP) (EC3.1.4.17; EC 3.1.4.53) and/or by directly inhibiting cAMP dependent protein kinase (PKA) (see for example, Han et al (2006) JBC 281 22 15050-15057). For example, a cAMP PDE or cAMP PDE fragment may (i) inhibit the catalytic (C) subunit of cAMP dependent protein kinase (PKA) (ii) catalyse the decomposition of cAMP, or (iii) both (i) and (ii).

Suitable cAMP PDEs are well-known in the art and include PDE1, PDE2, PDE3, PDE4, PDE7, PDE8, PDE10 and PDE11. In some preferred embodiments, the cAMP PDE may be PDE4 or PDE7.

PDE7 may include PDE7A (Gene ID 5150) and may comprise the amino acid sequence having the database reference CCDS56538.1; NP_001229247.1 GI: 334085277 (SEQ ID NO: 1) or CCDS34901.1; NP_002594.1 GI: 24429566.

PDE4 may include PDE4A (Gene ID 5141) and PDE4C (Gene ID 5143). PDE4A may comprise the amino acid sequence having the database reference CCDS45961.1; NP_001104777.1 GI: 162329608 (SEQ ID NO: 2) and PDE4C may comprise the amino acid sequence having the database reference CCDS12373.1; NP_000914.2 GI: 115529445 (SEQ ID NO: 3).

The amino acid sequences of other cAMP PDEs are well known in the art and available on public databases.

A cAMP PDE may comprise a cAMP PDE reference amino acid sequence cited herein or may be a variant thereof. A variant may have an amino acid sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity to the reference amino acid sequence.

Amino acid sequence identity is generally defined with reference to the algorithm GAP (GCG Wisconsin Package™, Accelrys, San Diego Calif.). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, psiBLAST or TBLASTN (which use the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), generally employing default parameters.

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, up to 15, up to 20, up to 30 or up to 40 residues may be inserted, deleted or substituted.

In some preferred embodiments, a variant may differ from a reference sequence by 1, 2, 3, 4, 5, 6, 7, 8, 9, 10 or more conservative substitutions. Conservative substitutions involve the replacement of an amino acid with a different amino acid having similar properties. For example, an aliphatic residue may be replaced by another aliphatic residue, a non-polar residue may be replaced by another non-polar residue, an acidic residue may be replaced by another acidic residue, a basic residue may be replaced by another basic residue, a polar residue may be replaced by another polar residue or an aromatic residue may be replaced by another aromatic residue. Conservative substitutions may, for example, be between amino acids within the following groups:

(i) alanine and glycine;
(ii) glutamic acid, aspartic acid, glutamine, and asparagine
(iii) arginine and lysine;
(iv) asparagine, glutamine, glutamic acid and aspartic acid
(v) isoleucine, leucine and valine;
(vi) phenylalanine, tyrosine and tryptophan
(vii) serine, threonine, and cysteine.

A fragment of a cAMP PDE is a truncated sequence which contains less than the full-length cAMP PDE sequence but which retains some or all of the cAMP signalling inhibition activity. A fragment may be a catalytic fragment that displays cAMP PDE activity or, more preferably a non-catalytic fragment, for example a fragment that inhibits cAMP dependent protein kinase (PKA). A fragment of a full-length cAMP PDE sequence may comprise at least 40 amino acids, at least 50 amino acids or at least 60 contiguous amino acids from the full-length cAMP PDE sequence. A fragment may comprise 60 or fewer, 100 or fewer, 200 or fewer or 300 or fewer amino acid residues.

In some embodiments, a cAMP PDE may bind and inhibit the catalytic (C) subunit of cAMP dependent protein kinase (PKA). A suitable fragment may comprise one or more copies of a 16-22 amino acid repeat sequence, preferably about 18 amino acids, comprising a PKA pseudosubstrate site, for example a RRGAI motif. A suitable repeat sequence may have the amino acid sequence;

P(V/N)P(Q/R)(H/Q)(V/L)(L/S)(S/Q)RRGAIS(F/Y)(S/S)SS (SEQ ID NO: 9)

Examples of repeat sequences are highlighted below in SEQ ID NO: 4. A fragment of a full-length cAMP PDE sequence may be an N terminal fragment i.e. the N terminal residue of the fragment may correspond to the N terminal residue of full-length cAMP PDE sequence. For example, an N terminal fragment may comprise at least 40, at least 50, at least 60, at least 75 or at least 100 contiguous amino acids from the N terminal of the full-length cAMP PDE sequence. In some embodiments, a suitable N terminal fragment may comprise amino acids 1 to 57 of SEQ ID NO: 4. In other embodiments, a suitable N terminal fragment may comprise SEQ ID NO: 4.

The recombinant cAMP PDE or fragments thereof expressed in the T cells may comprise a heterologous tag at the C terminal or more preferably the N terminal. A tag is a peptide sequence which is not naturally associated with the cAMP PDE and which forms one member of a specific binding pair. T cells that express the recombinant cAMP PDE may be identified and/or purified by the binding of the other member of the specific binding pair to the tag. For example, the tag may form an epitope which is bound by an anti-tag antibody. This may be useful in identifying modified T cells during treatment.

Suitable tags include for example, MRGS(H)$_6$ (SEQ ID NO: 10), DYKDDDDK (SEQ ID NO: 11) (FLAG™), T7-, S-(KETAAAKFERQHMDS) (SEQ ID NO: 12), poly-Arg (R$_{5-6}$) (SEQ ID NOS: 13-14), poly-His (H$_{2-10}$) (SEQ ID NOS: 15-21), poly-Cys (C$_4$) (SEQ ID NO: 22), poly-Phe (F$_{11}$) (SEQ ID NO: 23), poly-Asp(D$_{5-16}$) (SEQ ID NO: 24-35), SUMO tag (Invitrogen Champion pET SUMO expression system), Strept-tag II (WSHPQFEK) (SEQ ID NO: 40), c-myc (EQKLISEEDL) (SEQ ID NO: 36), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAEFRRQESDR (SEQ ID NO: 37), Santa Cruz Biotechnology Inc.) and Cruz tag 22™ (MRDALDRLDRLA (SEQ ID NO: 38), Santa Cruz Biotechnology Inc.). Known tag sequences are reviewed in Terpe (2003) Appl. Microbiol. Biotechnol. 60 523-533. In preferred embodiments, a haemagglutinin (HA) tag, such as YPYDVPDYA (SEQ ID NO: 39) may be used.

The cAMP PDE or fragment expressed in the modified T cell is a recombinant protein that is encoded by a heterologous nucleic acid i.e. the cAMP PDE is expressed from encoding nucleic acid that has been incorporated into the genome of the T cell by recombinant techniques. cAMP signalling in the modified T cells may be reduced relative to cAMP signalling in unmodified T cells. In some embodiments, cAMP PDE activity in the modified T cells may be at least 5 fold higher, at least 10 fold higher or at least 100 fold higher that cAMP PDE activity in unmodified T cells.

Modification of a T cell to express the cAMP PDE or fragment may comprise introducing the heterologous nucleic acid encoding the cAMP PDE or fragment into the T cell. Suitable methods for the introduction and expression of heterologous nucleic acids into T cells are well-known in the art and described in more detail below.

Following introduction, a modified T cell as described herein may comprise one or more than one copy of the heterologous nucleic acid encoding the cAMP PDE or fragment.

A modified T cell as described herein also expresses an antigen receptor that binds specifically to cancer cells.

The antigen receptor may be a T cell receptor (TCR). TCRs are disulphide-linked membrane anchored heterodimeric proteins, typically comprising highly variable alpha (α) and beta (β) chains expressed as a complex with invariant CD3 chain molecules. T cells expressing these type of TCRs are referred to as α:β (or αβ) T cells. A minority of T cells express an alternative TCR comprising variable gamma (γ) and delta (δ) chains and are referred to as γδ T cells.

Suitable TCRs bind specifically to a major histocompatibility complex (MHC) on the surface of cancer cells that displays a peptide fragment of a tumour antigen. An MHC is a set of cell-surface proteins which allow the acquired immune system to recognise 'foreign' molecules. Proteins are intracellularly degraded and presented on the surface of cells by the MHC. MHCs displaying 'foreign' peptides, such a viral or cancer associated peptides, are recognised by T cells with the appropriate TCRs, prompting cell destruction pathways. MHCs on the surface of cancer cells may display peptide fragments of tumour antigen i.e. an antigen which is present on a cancer cell but not the corresponding non-cancerous cell. T cells which recognise these peptide fragments may exert a cytotoxic effect on the cancer cell.

In some embodiments, the TCR that binds specifically to cancer cells may be naturally expressed by the T cells (i.e. an endogenous TCR). For example, the T cells may be Tumour Infiltrating Lymphocytes (TILs). TILs may be obtained from an individual with a cancer condition using standard techniques.

More preferably, the TCR is not naturally expressed by the T cells (i.e. the TCR is exogenous or heterologous). Heterologous TCRs may include αβTCR heterodimers. Suitable heterologous TCRs may bind specifically to cancer cells that express a tumour antigen. For example, the T cells may be modified to express a heterologous TCR that binds specifically to MHCs displaying peptide fragments of a tumour antigen expressed by the cancer cells in a specific cancer patient. Tumour antigens expressed by cancer cells in the cancer patient may identified using standard techniques.

A heterologous TCR may be a synthetic or artificial TCR i.e. a TCR that does not exist in nature. For example, a heterologous TCR may be engineered to increase its affinity or avidity for a tumour antigen (i.e. an affinity enhanced TCR). The affinity enhanced TCR may comprise one or more mutations relative to a naturally occurring TCR, for example, one or more mutations in the hypervariable complementarity determining regions (CDRs) of the variable regions of the TCR α and β chains. These mutations increase the affinity of the TCR for MHCs that display a peptide fragment of a tumour antigen expressed by cancer cells. Suitable methods of generated affinity enhanced TCRs include screening libraries of TCR mutants using phage or yeast display and are well known in the art (see for example Robbins et al J Immunol (2008) 180(9):6116; San Miguel et al (2015) Cancer Cell 28 (3) 281-283; Schmitt et al (2013) Blood 122 348-256; Jiang et al (2015) Cancer Discovery 5 901).

Preferred affinity enhanced TCRs may bind to cancer cells expressing one or more of the tumour antigens NY-ESO1, PRAME, alpha-fetoprotein (AFP), MAGE A4, MAGE A1, MAGE A10 and MAGE B2.

Alternatively, the antigen receptor may be a chimeric antigen receptor (CAR). CARs are artificial receptors that are engineered to contain an immunoglobulin antigen binding domain, such as a single-chain variable fragment (scFv). A CAR may, for example, comprise an scFv fused to a TCR CD3 transmembrane region and endodomain. An scFv is a fusion protein of the variable regions of the heavy ($V_H$) and light ($V_L$) chains of immunoglobulins, which may be connected with a short linker peptide of approximately 10 to 25 amino acids (Huston J. S. et al. Proc Natl Acad Sci USA 1988; 85(16):5879-5883). The linker may be glycine-rich for flexibility, and serine or threonine rich for solubility, and may connect the N-terminus of the $V_H$ to the C-terminus of the $V_L$, or vice versa. The scFv may be preceded by a signal peptide to direct the protein to the endoplasmic reticulum, and subsequently the T cell surface. In the CAR, the scFv may be fused to a TCR transmembrane and endodomain. A flexible spacer may be included between the scFv and the TCR transmembrane domain to allow for variable orientation and antigen binding. The endodomain is the functional signal-transmitting domain of the receptor. An endodomain of a CAR may comprise, for example, intracellular signalling domains from the CD3 ζ-chain, or from receptors such as CD28, 41BB, or ICOS. A CAR may comprise multiple signalling domains, for example, but not limited to, CD3z-CD28-41BB or CD3z-CD28-OX40.

The CAR may bind specifically to a tumour-specific antigen expressed by cancer cells. For example, the T cells may be modified to express a CAR that binds specifically to a tumour antigen that is expressed by the cancer cells in a specific cancer patient. Tumour antigens expressed by cancer cells in the cancer patient may identified using standard techniques.

Expression of a heterologous antigen receptor, such as a heterologous TCR or CAR, may alter the immunogenic specificity of the T cells so that they recognise or display improved recognition for one or more tumour antigens that are present on the surface of the cancer cells of an individual with cancer.

In some embodiments, the T cells may display reduced binding or no binding to cancer cells in the absence of the heterologous antigen receptor. For example, expression of the heterologous antigen receptor may increase the affinity and/or specificity of the cancer cell binding of modified T cells relative to unmodified T cells.

The term "heterologous" refers to a polypeptide or nucleic acid that is foreign to a particular biological system, such as a host cell, and is not naturally present in that system. A heterologous polypeptide or nucleic acid may be introduced to a biological system by artificial means, for example using recombinant techniques. For example, heterologous nucleic acid encoding a polypeptide may be inserted into a suitable expression construct which is in turn used to transform a host cell to produce the polypeptide. A heterologous polypeptide or nucleic acid may be synthetic or artificial or may exist in a different biological system, such as a different species or cell type. An endogenous polypeptide or nucleic acid is native to a particular biological system, such as a host cell, and is naturally present in that system. A recombinant polypeptide is expressed from heterologous nucleic acid that has been introduced into a cell by artificial means, for example using recombinant techniques. A recombinant polypeptide may be identical to a polypeptide that is naturally present in the cell or may be different from the polypeptides that are naturally present in that cell.

T cells may be modified to express a heterologous antigen receptor which specifically binds to the cancer cells of a cancer patient. The cancer patient may be subsequently treated with the modified T cells. Suitable cancer patients for treatment with the modified T cells may be identified by a method comprising;
  obtaining sample of cancer cells from an individual with cancer and;
  identifying the cancer cells as binding to the antigen receptor expressed by the modified T cells.

Cancer cells may be identified as binding to the antigen receptor by identifying one or more tumour antigens expressed by the cancer cells. Methods of identifying antigens on the surface of cancer cells obtained from an individual with cancer are well-known in the art.

In some embodiments, a heterologous antigen receptor suitable for the treatment of a specific cancer patient may be identified by;
  obtaining sample of cancer cells from an individual with cancer and;
  identifying an antigen receptor that specifically binds to the cancer cells.

An antigen receptor that specifically binds to the cancer cells may be identified for example by identifying one or more tumour antigens expressed by the cancer cells. Methods of identifying antigens on the surface of cancer cells obtained from an individual with cancer are well-known in the art. An antigen receptor which binds to the one or more tumour antigens or which binds to MHC-displayed peptide fragments of the one or more antigens may then be identified, for example from antigen receptors of known specificities or by screening a panel or library of antigen receptors with diverse specificities. Antigen receptors that specifically bind to cancer cells having one or more defined tumour antigens may be produced using routine techniques.

The T cells may be modified to express the identified antigen receptor as described herein.

The cancer cells of an individual suitable for treatment as described herein may express the antigen and may be of correct HLA type to bind the antigen receptor.

Cancer cells may be distinguished from normal somatic cells in an individual by the expression of one or more antigens (i.e. tumour antigens). Normal somatic cells in an individual may not express the one or more antigens or may express them in a different manner, for example at lower levels, in different tissue and/or at a different developmental stage. Tumour antigens may elicit immune responses in the individual. In particular, a tumour antigen may elicit a T cell-mediated immune response against cancer cells in the individual that express the tumour antigen. One or more tumour antigens expressed by cancer cells in a patient may be selected as a target antigen for heterologous receptors on modified T cells.

Tumour antigens expressed by cancer cells may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE and immunogenic fragments thereof (Simpson et al. Nature Rev (2005) 5, 615-625, Gure et al., Clin Cancer Res (2005) 11, 8055-8062; Velazquez et al., Cancer Immun (2007) 7, 1 1; Andrade et al., Cancer Immun (2008) 8, 2; Tinguely et al., Cancer Science (2008); Napoletano et al., Am J of Obstet Gyn (2008) 198, 99 e91-97).

Other tumour antigens include, for example, overexpressed, upregulated or mutated proteins and differentiation antigens particularly melanocyte differentiation antigens such as p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS and tyrosinase related proteins such as TRP-1, TRP-2.

Other tumour antigens include out-of-frame peptide-MHC complexes generated by the non-AUG translation initiation mechanisms employed by "stressed" cancer cells (Malarkannan et al. Immunity 1999 June; 10(6):681-90).

Other tumour antigens are well-known in the art (see for example WO00/20581; Cancer Vaccines and Immunotherapy (2000) Eds Stern, Beverley and Carroll, Cambridge University Press, Cambridge) The sequences of these tumour antigens are readily available from public databases but are also found in WO 1992/020356 A1, WO 1994/005304 A1, WO 1994/023031 A1, WO 1995/020974 A1, WO 1995/023874 A1 and WO 1996/026214 A1.

Preferred tumour antigens include NY-ESO1, PRAME, alpha-fetoprotein (AFP), MAGE A4, MAGE A1, MAGE A10 and MAGE B2, most preferably NY-ESO-1 and MAGE-A10.

NY-ESO-1 is a human tumour antigen of the cancer/testis (CT) family and is frequently expressed in a wide variety of cancers, including melanoma, prostate, transitional cell bladder, breast, lung, thyroid, gastric, head and neck, and cervical carcinoma (van Rhee F. et al. Blood 2005; 105(10): 3939-3944). In addition, expression of NY-ESO-1 is usually limited to germ cells and is not expressed in somatic cells (Scanlan M. J. et al. Cancer Immun. 2004; 4(1)). Suitable affinity enhanced TCRs that bind to cancer cells expressing NY-ESO-1 include NY-ESO-1$^{c259}$.

NY-ESO-1$^{c259}$ is an affinity enhanced TCR is mutated at positions 95 and 96 of the alpha chain 95:96LY relative to the wildtype TCR. NY-ESO-1$^{c259}$ binds to a peptide corresponding to amino acid residues 157-165 of the human cancer testis Ag NY-ESO-1 (SLLMWITQC) in the context of the HLA-A2+ class 1 allele with increased affinity relative to the unmodified wild type TCR (Robbins et al J Immunol (2008) 180(9):6116).

MAGE-A10 is a highly immunogenic member of the MAGE-A family of CT antigens, and is expressed in germ cells but not in healthy tissue. MAGE-A10 is expressed in high percentages of cancer cells from a number of tumours (Schultz-Thater E. et al. Int J Cancer. 2011; 129(5):1137-1148).

The modification of T cells and their subsequent expansion may be performed in vitro and/or ex vivo.

T cells may be modified to express a cAMP PDE or fragment of a cAMP PDE, and, optionally an antigen receptor, by the introduction of heterologous encoding nucleic acid into the T cells.

In some embodiments, heterologous nucleic acid encoding cAMP PDE or fragment of a cAMP PDE and antigen receptor are introduced into the T cells in the same expression vector. This may be helpful in increasing the proportion of T cells which express both genes after transduction. In other embodiments, heterologous nucleic acid encoding cAMP PDE and antigen receptor may be introduced into the T cells in different expression vectors.

The cAMP PDE or fragment and the antigen receptor may be expressed in the same transcript as a fusion protein and subsequently separated, for example using a site-specific protease. Alternatively, the cAMP PDE or fragment and the antigen receptor may be expressed in different transcripts.

For example, a fusion protein comprising truncated cAMP PDE and an NY-ESO TCR may be expressed. The fusion protein may comprise the amino acid sequence of SEQ ID NO: 6 or a variant thereof and may be encoded by a nucleic acid having the nucleotide sequence of SEQ ID NO: 5 or a variant thereof. Alternatively, a fusion protein comprising truncated cAMP PDE and an MAGE-A4 TCR may be expressed. The fusion protein may comprise the amino acid sequence of SEQ ID NO: 8 or a variant thereof and may be encoded by a nucleic acid having the nucleotide sequence of SEQ ID NO: 7 or a variant thereof.

Nucleic acid encoding an antigen receptor may encode all the sub-units of the receptor. For example, nucleic acid encoding a TCR may comprise a nucleotide sequence encoding a TCR α chain and a nucleotide sequence encoding a TCR β chain.

Nucleic acid may be introduced into the T cells by any convenient method. When introducing or incorporating a heterologous nucleic acid into a T cell, certain considerations must be taken into account, well-known to those skilled in the art. The nucleic acid to be inserted should be assembled within a construct or vector which contains effective regulatory elements which will drive transcription in the T cell. Suitable techniques for transporting the constructor vector into the T cell are well known in the art and include calcium phosphate transfection, DEAE-Dextran, electroporation, liposome-mediated transfection and transduction using retrovirus or other virus, e.g. vaccinia or lentivirus. For example, solid-phase transduction may be performed without selection by culture on retronectin-coated, retroviral vector-preloaded tissue culture plates.

Preferably, nucleic acid encoding a cAMP PDE or fragment and, optionally, an antigen receptor may be contained in a viral vector, most preferably a gamma retroviral vector or a lentiviral vector, such as a VSVg-pseudotyped lentiviral vector. The T cells may be transduced by contact with a viral particle comprising the nucleic acid. Viral particles for transduction may be produced according to known methods. For example, HEK293T cells may be transfected with plasmids encoding viral packaging and envelope elements as well as a lentiviral vector comprising the coding nucleic acid. A VSVg-pseudotyped viral vector may be produced in combination with the viral envelope glycoprotein G of the Vesicular stomatitis virus (VSVg) to produce a pseudotyped virus particle.

Many known techniques and protocols for manipulation and transformation of nucleic acid, for example in preparation of nucleic acid constructs, introduction of DNA into cells and gene expression are described in detail in *Protocols in Molecular Biology*, Second Edition, Ausubel et al. eds. John Wiley & Sons, 1992.

Following the introduction of nucleic acid into the T cells, the initial population of modified T cells may be cultured in vitro such that the modified T cells proliferate and expand the population.

The modified T cell population may for example be expanded using magnetic beads coated with anti-CD3 and anti-CD28. The modified T cells may be cultured using any convenient technique to produce the expanded population. Suitable culture systems include stirred tank fermenters, airlift fermenters, roller bottles, culture bags or dishes, and other bioreactors, in particular hollow fibre bioreactors. The use of such systems is well-known in the art.

Numerous culture media suitable for use in the proliferation of T cells ex vivo are available, in particular complete media, such as AIM-V, Iscoves medium and RPMI-1640 (Invitrogen-GIBCO). The medium may be supplemented with other factors such as serum, serum proteins and selective agents. For example, in some embodiments, RPMI-1640 medium containing 2 mM glutamine, 10% FBS, 25 mM HEPES, pH 7.2, 1% penicillin-streptomycin, and 55 µM β-mercaptoethanol and optionally supplemented with 20 ng/ml recombinant IL-2 may be employed. The culture medium may be supplemented with the agonistic or antagonist factors described above at standard concentrations which may readily be determined by the skilled person by routine experimentation.

Conveniently, cells are cultured at 37° C. in a humidified atmosphere containing 5% $CO_2$ in a suitable culture medium.

Methods and techniques for the culture of T cells and other mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52).

In some embodiments, it may be convenient to isolate and/or purify the modified T cells from the population. Any convenient technique may be used, including FACS and antibody coated magnetic particles.

Optionally, the population of modified T cells produced as described herein may be stored, for example by lyophilisation and/or cryopreservation, before use.

A population of modified T cells may be admixed with other reagents, such as buffers, carriers, diluents, preservatives and/or pharmaceutically acceptable excipients. Suitable reagents are described in more detail below. A method described herein may comprise admixing the population of modified T cells with a pharmaceutically acceptable excipient.

Pharmaceutical compositions suitable for administration (e.g. by infusion), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Suitable vehicles can be found in standard pharmaceutical texts, for example, Remington's Pharmaceutical Sciences, 18th edition, Mack Publishing Company, Easton, Pa., 1990.

In some preferred embodiments, the modified T cells may be formulated into a pharmaceutical composition suitable for intravenous infusion into an individual.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

An aspect of the invention provides a population of modified T cells expressing a recombinant cAMP PDE or fragment thereof and an antigen receptor which binds specifically to cancer cells. A suitable population may be produced by a method described above.

The population of modified T cells may be for use as a medicament. For example, a population of modified T cells as described herein may be used in cancer immunotherapy therapy, for example adoptive T cell therapy.

Other aspects of the invention provide the use of a population of modified T cells as described herein for the manufacture of a medicament for the treatment of cancer, a population of modified T cells as described herein for the treatment of cancer, and a method of treatment of cancer may comprise administering a population of modified T cells as described herein to an individual in need thereof.

The population of modified T cells may be autologous i.e. the modified T cells were originally obtained from the same individual to whom they are subsequently administered (i.e. the donor and recipient individual are the same). A suitable population of modified T cells for administration to the individual may be produced by a method comprising providing an initial population of T cells obtained from the individual, modifying the T cells to express a cAMP PDE or fragment thereof and an antigen receptor which binds specifically to cancer cells in the individual, and culturing the modified T cells.

The population of modified T cells may be allogeneic i.e. the modified T cells were originally obtained from a different individual to the individual to whom they are subsequently administered (i.e. the donor and recipient individual are different). The donor and recipient individuals may be HLA matched to avoid GVHD and other undesirable immune effects. A suitable population of modified T cells for administration to a recipient individual may be produced by a method comprising providing an initial population of T cells obtained from a donor individual, modifying the T cells to express a cAMP PDE or fragment thereof and an antigen receptor which binds specifically to cancer cells in the recipient individual, and culturing the modified T cells.

Following administration of the modified T cells, the recipient individual may exhibit a T cell mediated immune response against cancer cells in the recipient individual. This may have a beneficial effect on the cancer condition in the individual.

Cancer conditions may be characterised by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

Cancer cells within an individual may be immunologically distinct from normal somatic cells in the individual (i.e. the cancerous tumour may be immunogenic). For example, the cancer cells may be capable of eliciting a systemic immune response in the individual against one or more antigens expressed by the cancer cells. The tumour antigens that elicit the immune response may be specific to cancer cells or may be shared by one or more normal cells in the individual.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment may also be prophylactic (i.e. prophylaxis). For example, an individual susceptible to or at risk of the occurrence or re-occurrence of cancer may be treated as described herein. Such treatment may prevent or delay the occurrence or re-occurrence of cancer in the individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of T cells, and a decrease in levels of tumour-specific antigens. Administration of T cells modified as described herein may improve the capacity of the individual to resist cancer growth, in particular growth of a cancer already present the subject and/or decrease the propensity for cancer growth in the individual.

The modified T cells or the pharmaceutical composition comprising the modified T cells may be administered to a subject by any convenient route of administration, whether systemically/peripherally or at the site of desired action, including but not limited to; parenteral, for example, by infusion. Infusion involves the administration of the T cells in a suitable composition through a needle or catheter. Typically, T cells are infused intravenously or subcutaneously, although the T cells may be infused via other non-oral routes, such as intramuscular injections and epidural routes. Suitable infusion techniques are known in the art and commonly used in therapy (see, e.g., Rosenberg et al., New Eng. J. of Med., 319:1676, 1988).

Typically, the number of cells administered is from about $10^5$ to about $10^{10}$ per Kg body weight, typically $2 \times 10^8$ to $2 \times 10^{10}$ cells per individual, typically over the course of 30 minutes, with treatment repeated as necessary, for example at intervals of days to weeks. It will be appreciated that appropriate dosages of the modified T cells, and compositions comprising the modified T cells, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular cells, the route of administration, the time of administration, the rate of loss or inactivation of the cells, the duration of the treatment, other drugs, compounds, and/or materials used in combination, and the age, sex, weight, condition, general health, and prior medical history of the patient. The amount of cells and the route of administration will ultimately be at the discretion of the physician, although generally the dosage will be to achieve local concentrations at the site of action which achieve the desired effect without causing substantial harmful or deleterious side-effects.

While the modified T cells may be administered alone, in some circumstances the modified T cells may be administered cells in combination with the target antigen, APCs displaying the target antigen, and/or IL-2 to promote expansion in vivo of the population of modified T cells.

The population of modified T cells may be administered in combination with one or more other therapies, such as cytokines e.g. IL-2, cytotoxic chemotherapy, radiation and immuno-oncology agents, including checkpoint inhibitors, such as anti-B7-H3, anti-B7-H4, anti-TIM3, anti-KIR, anti-LAG3, anti-PD-1, anti-PD-L1, and anti-CTLA4 antibodies.

The one or more other therapies may be administered by any convenient means, preferably at a site which is separate from the site of administration of the modified T cells.

Administration of modified T cells can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. Preferably, the modified T cells are administered in a single transfusion of a least $1 \times 10^9$ T cells.

Other aspects of the invention provide nucleic acids and other reagents for the generation of modified T cells as described herein.

An isolated nucleic acid may comprise a nucleotide sequence encoding an antigen receptor which binds specifically to cancer cells and a nucleotide sequence encoding a cAMP PDE or a fragment of a cAMP PDE.

The coding sequences may be operably linked to the same or different promoters or other regulatory elements. Suitable promoters are well known in the art and include mammalian promoters, such as Human elongation factor-1 alpha (EF1α). In some embodiments, the coding sequences may be separated by a cleavage recognition sequence. This allows the cAMP PDE or fragment and antigen receptor to be expressed as a single fusion which undergoes intracellular cleavage by a site specific protease, such as furin, to generate the two separate proteins. Suitable cleavage recognition sequences include 2A-furin sequence. Examples of single fusions include SEQ ID NO: 6, which comprises a MAGE-A4 TCR and an N terminal PDE7A fragment separated by a furin cleavage site; and SEQ ID NO: 8, which comprises a NY-ESO TCR and an N terminal PDE7A fragment separated by a furin cleavage site.

Examples of suitable isolated nucleic acids include SEQ ID NO: 5, which encodes a fusion comprising a MAGE-A4 TCR and an N terminal PDE7A fragment separated by a furin cleavage sequence; and SEQ ID NO: 7, which encodes a fusion comprising an NY-ESO TCR and an N terminal PDE7A fragment separated by a furin cleavage site.

The nucleotide sequences encoding the antigen receptor and the cAMP PDE or fragment may be located in the same expression vector. For example, a suitable expression vector may comprise a nucleic acid as described above. Alternatively, the coding sequences may be located in separate expression vectors.

Suitable vectors are well known in the art and are described in more detail above.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as E. coli. Preferred vectors include retroviral vectors, such as lentiviral vectors, including VSVg-pseudotyped self-inactivating vectors.

A viral vector, such as a lentivirus, may be contained in a viral particle comprising the nucleic acid vector encapsulated by one or more viral proteins. A viral particle may be produced by a method comprising transducing mammalian cells with a viral vector as described herein and one or more viral packaging and envelope vectors and culturing the transduced cells in a culture medium, such that the cells produce lentiviral particles that are released into the medium.

Following release of viral particles, the culture medium comprising the viral particles may be collected and, optionally the viral particles may be concentrated.

Following production and optional concentration, the viral particles may be stored, for example by freezing at −80° C. ready for use in transducing T cells.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

Experiments

1. Materials and Methods
1.1 Lentiviral Vectors and Viral Particle Production

The lentiviral system was a $3^{rd}$ generation VSVg-pseudotyped self-inactivating vector used to express phosphodiesterase (PDE) 4C or PDE7A containing an N-terminal human Influenza hemagglutinin tag or PDE7A or a fragment of PDE7A all in tandem with the NY-ESO1$^{c259}$ TCR α- and β-chains from the EF1α promoter. Each transgene was separated by a 2A-furin sequence.

Figure 1B:
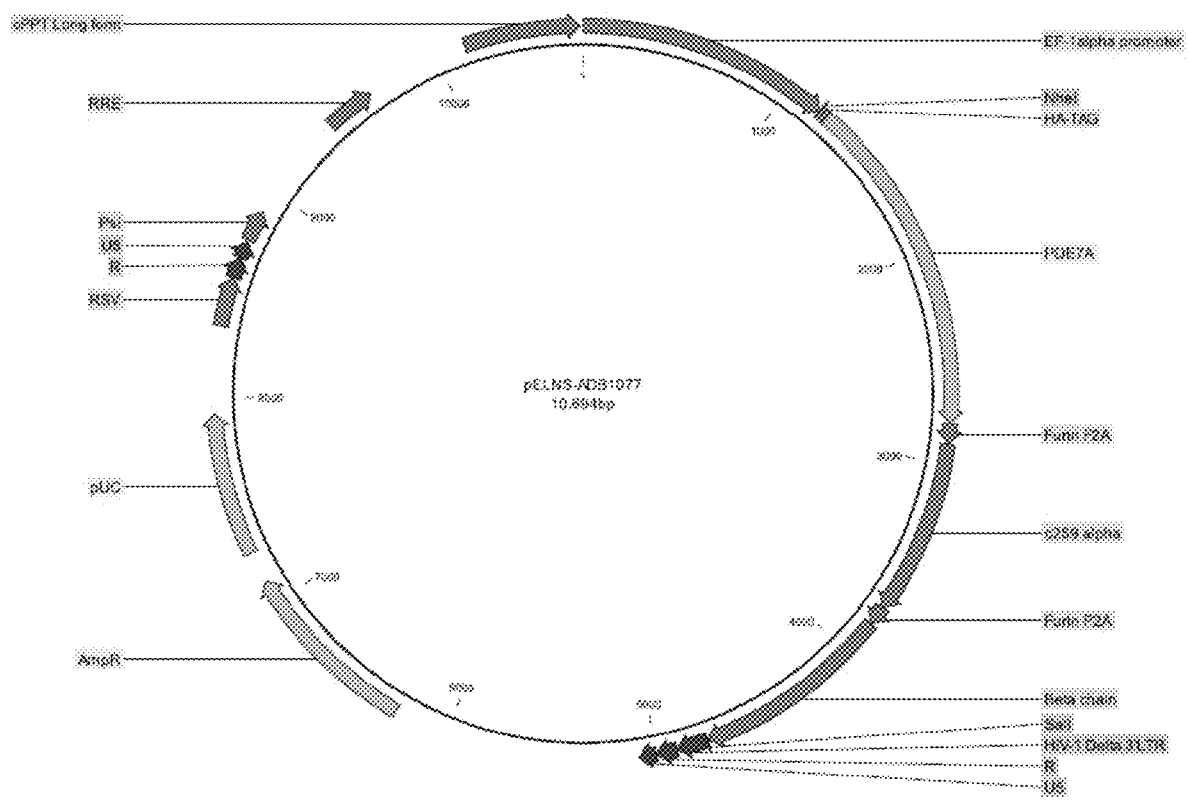

The plasmid pELNS-ADB1076 comprises a PDE4C (FIG. 1A) or PDE7A (FIG. 1B) upstream of the TCR. In addition to the EF-1a promoter and downstream PDE and TCR transgenes, various elements representing lentivirus and bacterial plasmid features are shown. Maps were generated with the CLC Main Workbench software version 7.6.1.

Lentiviral particles were produced by transfecting HEK 293T cells with a 3 plasmid system encoding the packaging and envelope elements as well as the lentivector plasmid using the Turbofect transfection reagent (ThermoScientific). Supernatants were collected 48-72 hours after transfection, centrifuged and filtered prior to overnight concentration at 10,000×g. Medium was removed so that lentiviral particles were concentrated 5-10-fold compared with the unconcentrated supernatants. Lentivirus preparations were then snap-frozen on dry ice and stored at −80° C. until used.

1.2 PBMC Isolation and T Cell Expansion

PBMCs isolated from the venous blood of healthy human volunteers were subjected to CD14+ cell depletion, incubated overnight with CD3/CD28 antibody coated beads overnight in IMDM medium (Gibco) supplemented with 10% foetal bovine serum (FBS), 1% penicillin and streptomycin and 1% L-glutamine in the presence of IL-2, followed by lentiviral transduction to express either the enhanced affinity NY-ESO1$^{c259}$ TCR or the NY-ESO1$^{c259}$ TCR expressed in tandem with HA-PDE7A, HA-PDE4C, PDE7A or a fragment of PDE7A. T cells were then expanded in culture for 14 days and TCR transduction levels were assessed by flow cytometry by staining for Vβ13.1 (TRBV 6-9).

Lentiviral transduction was performed using the 4 vector system described in Dull, T., et al (1998). J. Virol. 72, 8463-8471.

1.3 Cancer Cells

NY-ESO1-positive A375 melanoma cells purchased from the ATCC (CRL-1619) were cultured in RPMI 1640 (Gibco) supplemented with 10% FBS, 1% penicillin and streptomycin and 1% L-glutamine (R10). A375 melanoma cells were harvested using Trypsin/0.25% EDTA and washed prior to use as targets in T cell activation assays.

1.4 Reagents

Adenosine, prostaglandin E2 (PGE2) and forskolin were purchased from Sigma Aldrich. Adenosine powder was diluted in 0.13 M $NH_4OH$ diluted in PBS to a final concentration of 25 mM. Forskolin was diluted in dimethyl-sulfoxide (DMSO) at 100 mM. Prostaglandin E2 was diluted in PBS containing 10% ethanol at 285 μM. Each reagent was used at the final concentrations indicated in section 2.

1.5 IFN-γ ELISA Assay and Cytokine Measurement

A375 melanoma target cells were harvested, resuspended and plated out in 96 well flat bottom plates at 50,000 target cells/well. T cells were either used fresh following expansion or cryopreserved, thawed and washed. T cells were rested for approximately 2 hours at 37° C. in R10 medium, before plating out at a concentration of 120,000-200,000 T cells/well.

Adenosine, PGE2 or forskolin were added at the indicated final concentration to make the final volume to 200 μl/well. Each assay condition was performed in triplicates. Cells were cultured for 48 hours at 37° C. and supernatants were collected before freezing and storing at −20° C. Prior to any assay, the plates were thawed before centrifuging. Supernatants were then transferred to new 96 well plates for subsequent use in assays.

IFN-γ concentrations were determined using the human DuoSet ELISA kits (R&D Systems) according to the manufacturer's instructions using 96 well half area plates. The assays were developed using commercial TMB substrate solution and the reaction stopped with 1M $H_2SO_4$. Assays were read using the Spectrostar Omega at 450 nm with wavelength correction set to 540 nm. Data were analysed using Spectrostar data analysis software.

1.6 Time-Resolved Cytotoxicity Assays

IncuCyte™ FLR technology (Essen Bioscience) enables direct visualisation of caspase-3/7 dependent apoptosis by microscopy at 37° C. in real time. Kinetic measurement of apoptosis is made using CellPlayer™ 96-Well Kinetic Caspase-3/7 reagent (Essen Biosciences) which couples the activated caspase-3/7 recognition motif (DEVD) to Nuncview™ 488, a DNA intercalating dye. When added to tissue culture medium, this inert and non-fluorescent substrate crosses the cell membrane where it is cleaved by activated caspase-3/7 resulting in the release of the DNA dye and green fluorescent staining of the nuclear DNA. Kinetic activation of caspase-3/7 can be monitored morphologically using live cell imaging, and quantified using IncuCyte object counting algorithm as the number of fluorescent objects per $mm^2$. Apoptotic T cells are gated out the analysis by size exclusion setting filter threshold at 100 μm$^2$.

IncuCyte assays were carried out as follows. Briefly, 24 hours prior to assay set up, A375 melanoma target cells were plated at 15,000-20,000 cells per well in 50 μl R10. On the day of the assay, prior to adding the effector cells, 50 μl per well of assay medium containing 10 μM CellPlayer™ 96-Well Kinetic Caspase-3/7 reagent in the presence or absence of forskolin or PGE2. Non-transduced and transduced effector cells were plated at 60,000 cells per well in 50 μl assay medium, in triplicate wells, to give a final volume of 150 μl. The IncuCyte was set to take images of each well using a 10-fold magnification every 3-4 hours over 96 hours (4 days) at 37° C./5% $CO_2$.

2. Results
2.1 Target Cell Killing Kinetics of T Cells Expressing NY-ESO1$^{c259}$ and PDE7A The ability of T cells expressing NY-ESO1$^{c259}$ TCR or NY-ESO1$^{c259}$ TCR in tandem with HA-PDE7A to induce apoptosis of A375 target cells was measured by time-resolved cytotoxicity assay. 60,000 T cells with different transduction states (Non-transduced (NTDs), c259 TCR (ADB869), c259 TCR+PDE7A (ADB1077)) were added to each assay well and co-incubated with HLA-A2+/NYESO+ A375 melanoma target cells seeded at 15,000 cells per well 24 hours prior to the assay. CellPlayer™ 96-Well Kinetic Caspase-3/7 reagent was added to all wells at a final concentration of 3.3 μM. Images were taken at intervals of 4 hours over a duration of 96 hours. The number of objects/$mm^2$, a measure of target cells undergoing apoptosis, was determined for each image and plotted against time.

Figure 2A:
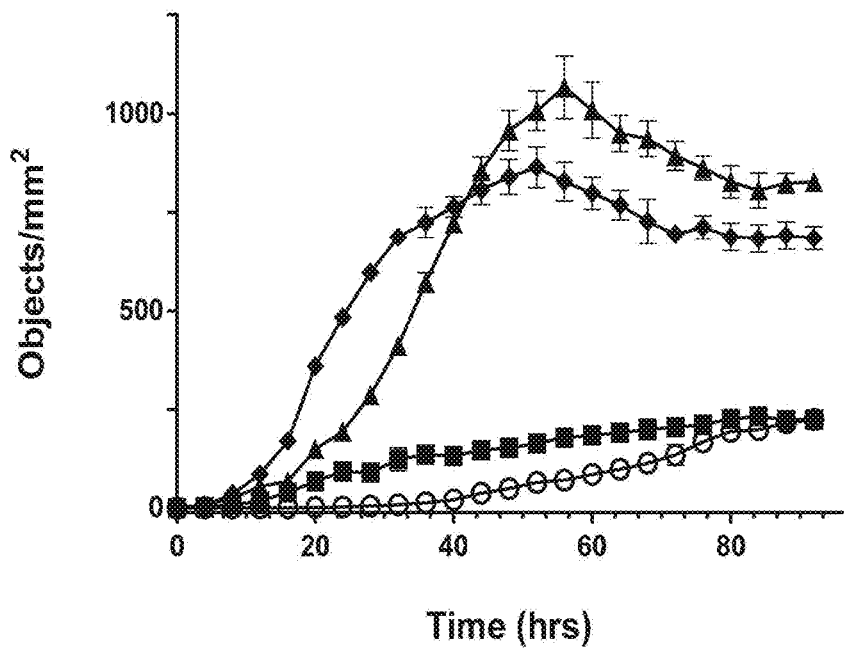
FIGS. 2A and 2B show target cell killing kinetics by NY-ESO specific T cells that overexpress PDE7A.
Figure 2B:
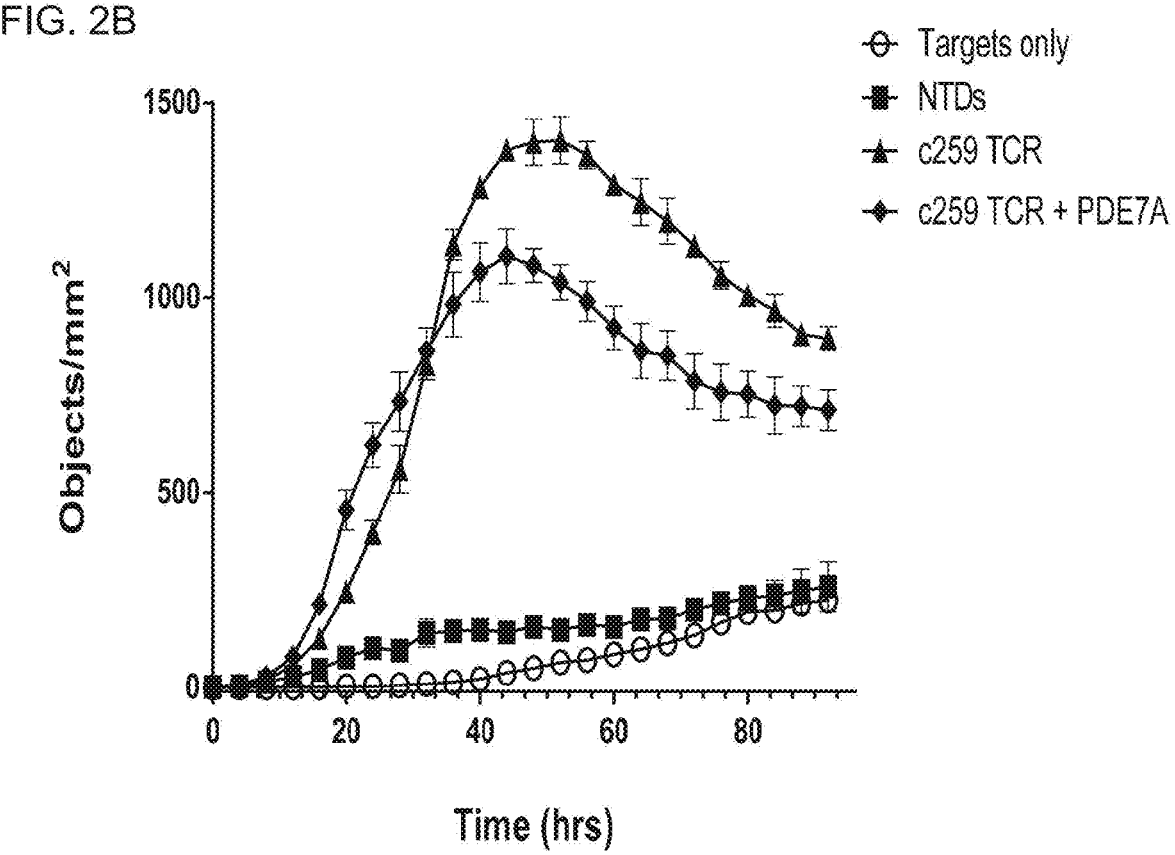

T cells transduced with NY-ESO1$^{c259}$ TCR in tandem with HA-PDE7A showed an improved basal ability to induce apoptosis in A375 target cells (FIGS. 2A and 2B). Data points show mean values and standard error to the mean of triplicate wells. FIGS. 2A and 2B represent experiments performed with T cells isolated from 2 healthy donors. Data shown are representative of 5 different experiments.

2.2 Target Cell Killing Kinetics of T Cells Expressing NY-ESO1$^{c259}$ and PDE7A in the Presence of PGE2

The ability of T cells expressing NY-ESO1$^{c259}$ TCR or NY-ESO1$^{c259}$ TCR in tandem with HA-PDE7A to induce apoptosis of A375 target cells was measured by time-resolved cytotoxicity assay in the absence and presence of prostaglandin E2.

60,000 T cells with different transduction status were added to each assay well and co-incubated with HLA-A2+/NYESO+A375 melanoma target cells seeded at 15,000 per well 24 hours prior to the assay. Prostaglandin E2 was added at a final concentration of 1 µM in each well. CellPlayer™ 96-Well Kinetic Caspase-3/7 reagent was added to all wells at a final concentration of 3.3 µM. Images were taken at intervals of 4 hours over a duration of 96 hours. The number of objects/mm$^2$, a measure of target cells undergoing apoptosis, was determined for each image and plotted against time.

Figure 3A:
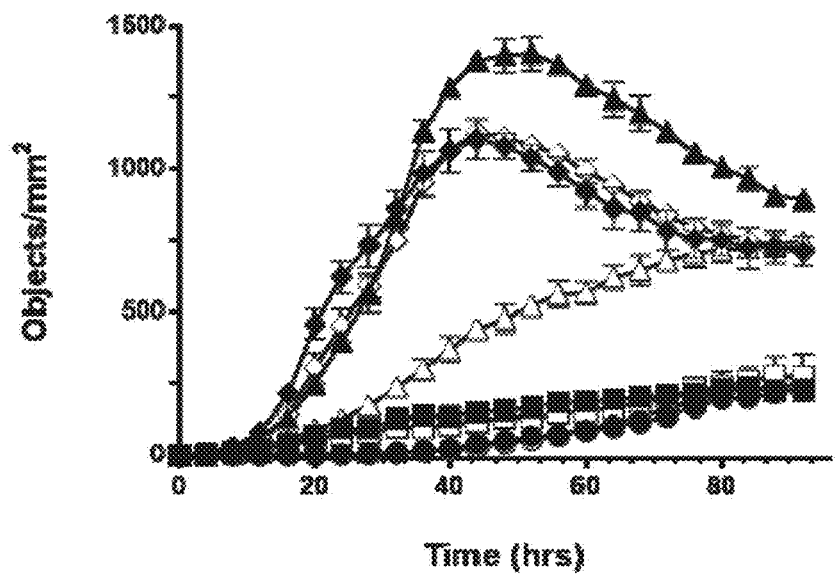
FIGS. 3A and 3B show that overexpression of PDE7A in NY-ESO specific T cells confers resistance to inhibitory effects of prostaglandin E2.
Figure 3B:
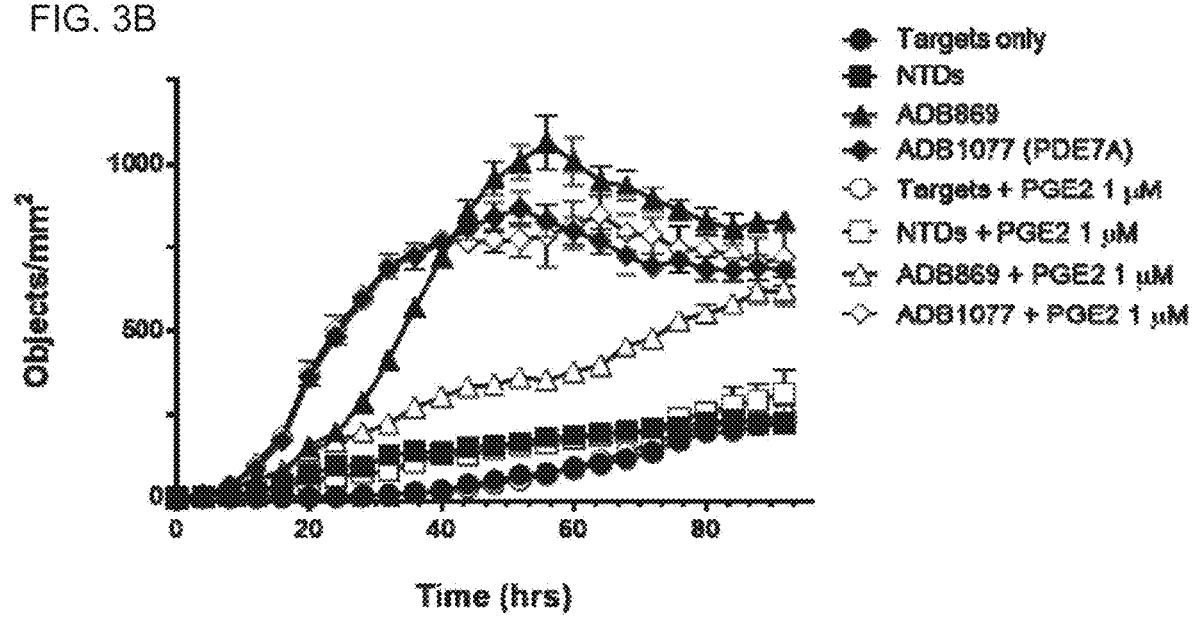

Target A375 cells alone, non-transduced cells (NTDs), T cells expressing NY-ESO1$^{c259}$ TCR (ADB869), and T cells expressing both NY-ESO1$^{c259}$ TCR and PDE7A (ADB1077) were investigated for their ability to induce apoptosis of the target cells in the absence (closed symbols) or presence (open symbols) of PGE2. The overexpression of PDE7A in NY-ESO specific T cells confers resistance to the inhibitory effects of PGE2 (FIGS. 3A and 3B). The T cells transduced with PDE7A showed killing kinetics with PGE2 present similar to that shown by PDE7A/NY-ESO1$^{c259}$ TCR T cells in the absence of PGE2.

Data points show mean values and standard error to the mean of triplicate wells. FIGS. 3A and 3B represent experiments performed with T cells isolated from 2 healthy donors. Data shown are representative of 6 experiments.

2.3 Target Cell Killing Kinetics of T Cells Expressing NY-ESO1$^{c259}$ and PDE7A in the Presence of Forskolin The ability of T cells expressing NY-ESO1$^{c259}$ TCR or NY-ESO1$^{c259}$ TCR in tandem with HA-PDE7A to induce apoptosis of A375 target cells was measured by time-resolved cytotoxicity assay in the absence and presence of forskolin.

60,000 T cells with different transduction status, as indicated in the key, were added to each assay well and co-incubated with HLA-A2+/NYESO+A375 melanoma target cells seeded at 15,000 per well 24 hours prior to the assay. Forskolin was added at a final concentration of 30 µM in each well. CellPlayer™ 96-Well Kinetic Caspase-3/7 reagent was added to all wells at a final concentration of 3.3 µM. Images were taken at intervals of 4 hours over a duration of 96 hours. The number of objects/mm$^2$, a measure of target cells undergoing apoptosis, was determined for each image and plotted against time.

Figure 4A:
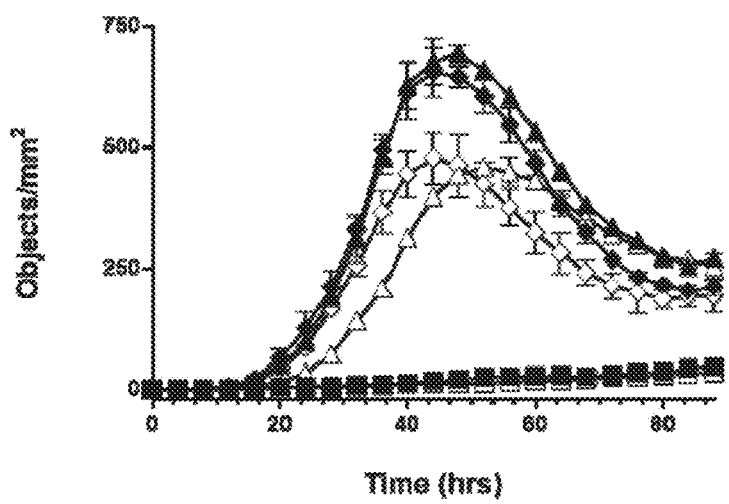
FIGS. 4A and 4B show that overexpression of PDE7A in NY-ESO specific T cells confers partial resistance to the inhibitory effects of forskolin on T cell killing ability.
Figure 4B:
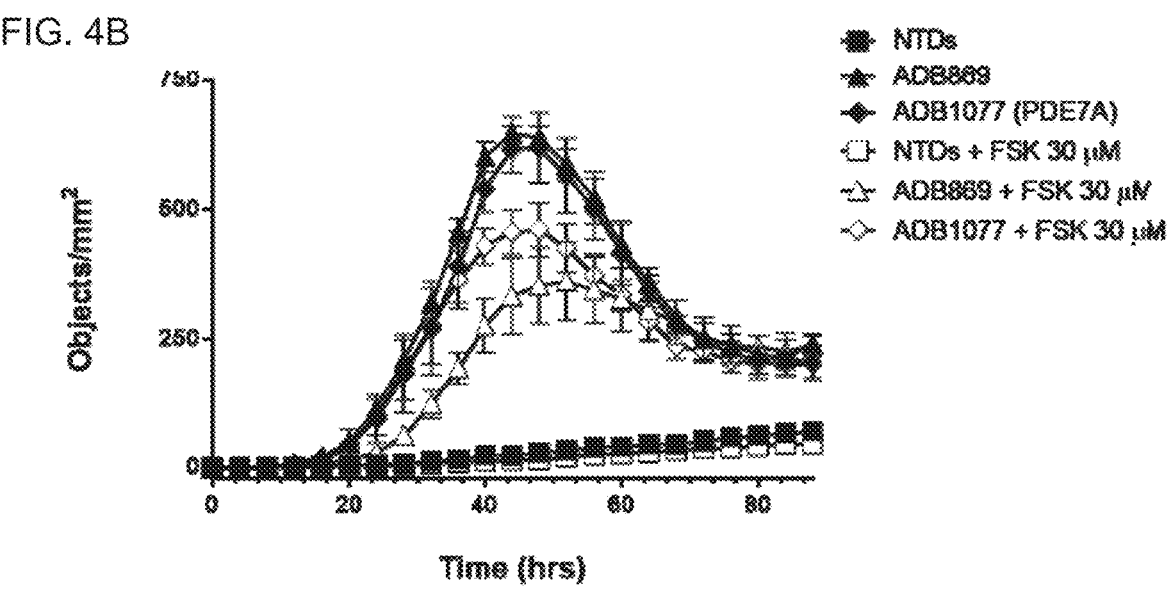

Non-transduced cells (NTDs), T cells expressing NY-ESO1$^{c259}$ TCR (ADB869), and T cells expressing both NY-ESO1$^{c259}$ TCR and PDE7A (ADB1077) were investigated for their ability to induce apoptosis of the target cells in the absence (closed symbols) or presence (open symbols) of forskolin. The overexpression of PDE7A in NY-ESO specific T cells confers partial resistance to the inhibitory effects of forskolin on target cell killing ability (FIGS. 4A and 4B). Data points show mean values and standard error to the mean of triplicate wells. FIGS. 4A and 4B represent experiments performed with T cells isolated from 2 healthy donors. Data shown are representative of 6 different experiments.

2.4 IFN-γ Secretion of T Cells Expressing NY-ESO1$^{c259}$ and PDE7A

Forskolin, adenosine and PGE2 can increase intracellular cAMP levels. To investigate the effect of these mediators on IFN-γ secretion from T cells, cytokine analysis was performed on T cells expressing NY-ESO1$^{c259}$ TCR and T cells expressing both NY-ESO1$^{c259}$ TCR and PDE7A by sandwich ELISA.

200,000 T cells isolated from a healthy donor transduced with lentivectors expressing the NY-ESO1-specific TCR c259 alone or in tandem with phosphodiesterase 7A (PDE7A) were added to each assay well and co-incubated with HLA-A2+/NYESO+A375 melanoma target cells seeded at 50,000 per well. Forskolin was added at a final concentration of 30 µM adenosine at 250 µM and prostaglandin E2 at 1 or 0.3 µM. T cells and target cells were co-cultured for 48 hours and the supernatants were collected for cytokine analysis.

Figure 5A:
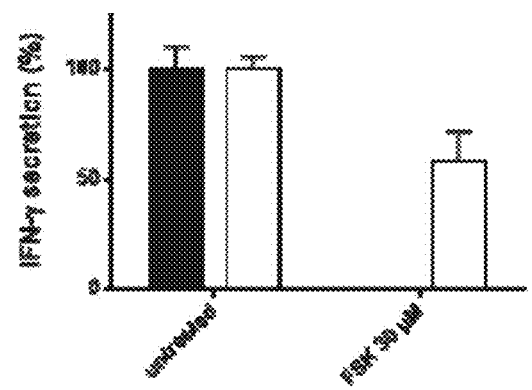
FIGS. 5A and 5B and 5C show that NY-ESO specific T cells overexpressing PDE7A are partially resistant to the inhibition of cytokine release by mediators that increase intracellular cAMP. Overexpression of PDE7A in NY-ESO specific T cells partially overcomes the inhibitory effects of forskolin (FIG. 5A), adenosine (FIG. 5B) and PGE2 (FIG. 5C) on IFN-γ secretion.
Figure 5B:
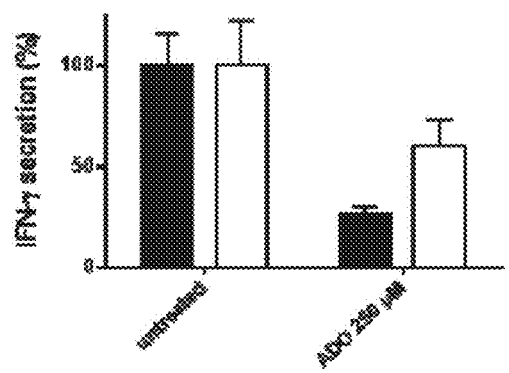
Figure 5C:
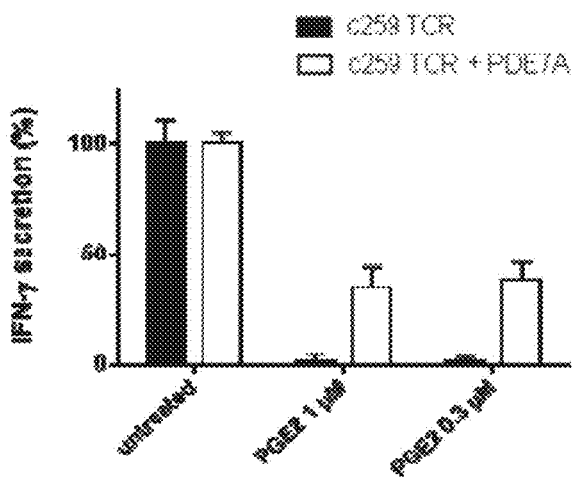

T cells expressing PDE7A are partially resistant to the inhibition of IFN-γ release by forskolin (FIG. 5A), adenosine (FIG. 5B), and PGE2 (FIG. 5C). Data shown are representative of 6 experiments.

2.5 IFN-γ Secretion of T Cells Expressing NY-ESO1$^{c259}$ and PDE4C

Sandwich ELISA was employed to investigate the effect of forskolin and PGE2 on IFN-γ secretion from T cells expressing NY-ESO1$^{c259}$ TCR and T cells expressing both NY-ESO1$^{c259}$ TCR and PDE4C.

200,000 T cells isolated from a healthy donor transduced with lentivectors expressing the NY-ESO1-specific TCR c259 alone or in tandem with phosphodiesterase 4C (PDE4C) were added to each assay well and co-incubated with HLA-A2+/NYESO+A375 melanoma target cells seeded at 50,000 per well. Forskolin was added at a final concentration of 30 µM and prostaglandin E2 at 1 µM. T cells and target cells were co-cultured for 48 hours and the supernatants were collected for cytokine analysis.

Figure 6A:
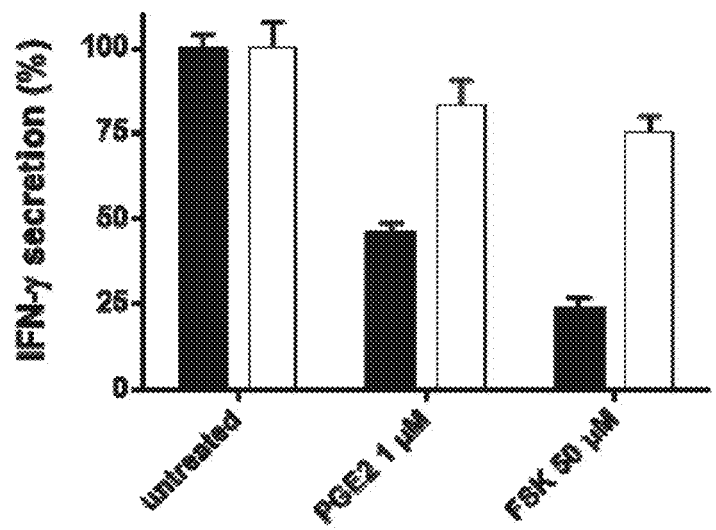
FIGS. 6A and 6B show that NY-ESO specific T cells overexpressing PDE4C are partially resistant to the inhibition of cytokine release by mediators that increase intracellular cAMP.
Figure 6B:
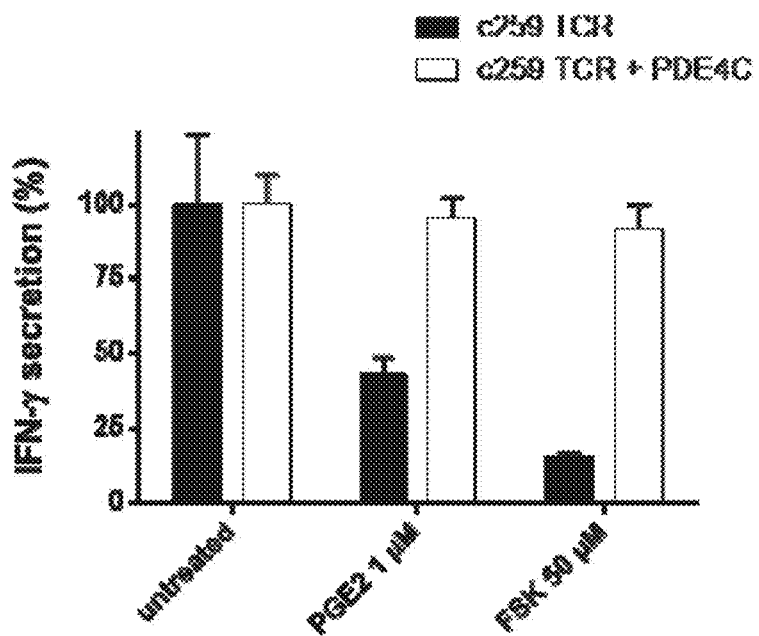

T cells expressing PDE4C show partial resistance to the inhibitory effects of PGE2 and forskolin on IFN-γ release (FIGS. 6A and 6B). FIGS. 6A and 6B represent experiments performed with T cells isolated from 2 healthy donors.

2.6 Biological Titre of Lentiviral Constructs Containing NY-ESO1$^{c259}$ TCR and Full-Length or Truncated Forms of PDE7A The various lentiviral preparations were titrated on PBL to determine their effective biological titre. T cell transduction levels were determined by staining for the Vβ chain of the TCR (Vβ13.1).

Figure 7:
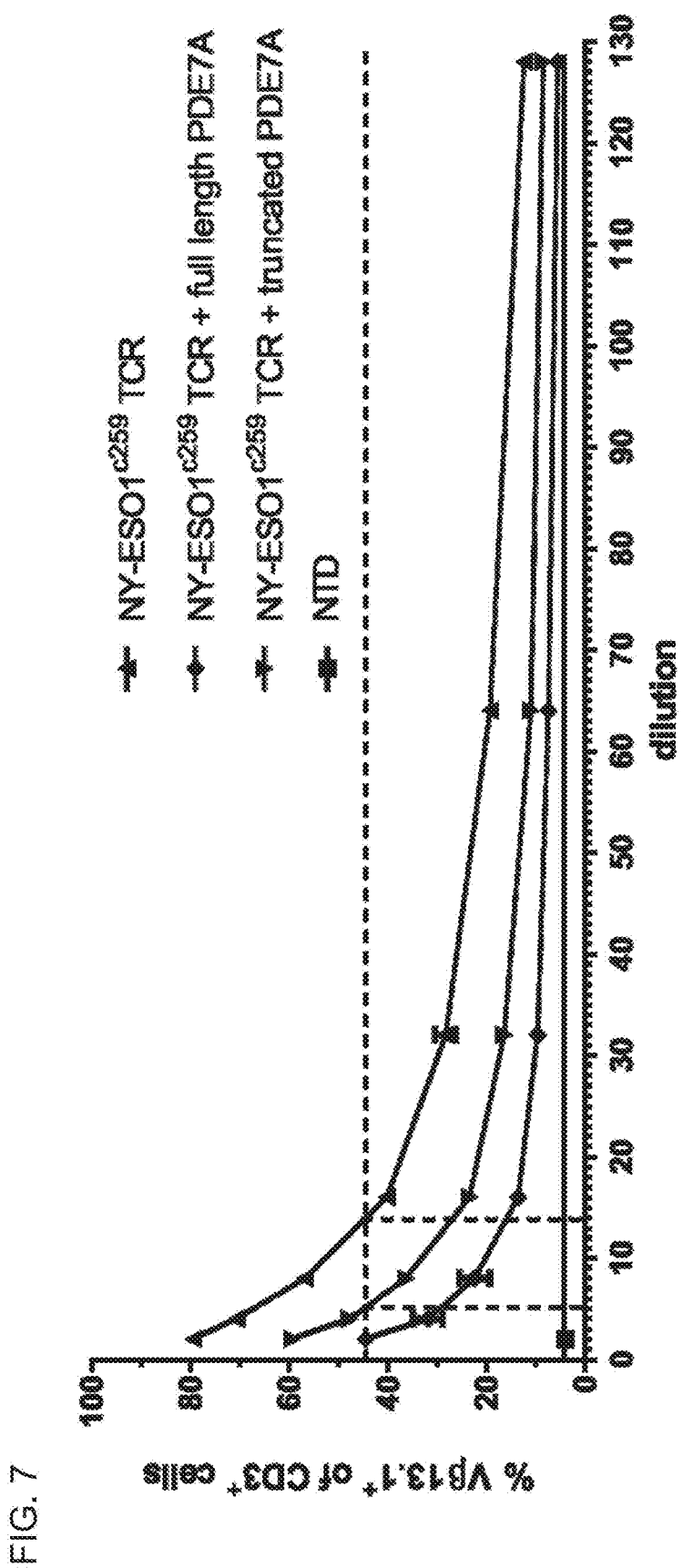
FIG. 7 shows the results of a lentiviral transduction using the NY-ESO receptor alone (NY-ESO1$^{c259}$ TCR), NY-ESO receptor in combination with full-length PDE7A (NY-ESO1$^{c259}$ TCR+full length PDE7A) and NY-ESO receptor in combination with truncated PDE7A (NY-ESO1$^{c259}$ TCR+truncated PDE7A).

When using the same concentration of lentivirus, T cell transduction was always much lower for the NY-ESO1$^{c259}$ TCR+ full length PDE7A transduced cells compared to cells transduced with NY-ESO1$^{c259}$ TCR alone, while the transduction was at an intermediate level for NY-ESO1$^{c259}$ TCR+ truncated PDE7A transduced cells (FIG. 7). The differences in transduction efficiency can probably be explained by the different sizes of the constructs.

Figure 8A:
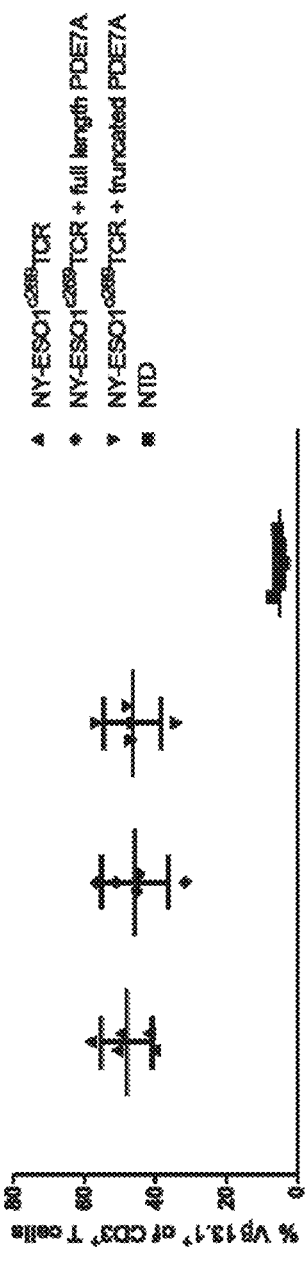
FIGS. 8A and 8B show the transduction efficiency and TCR expression levels for NY-ESO TCRs following transduction with full-length and truncated PDE7A.
Figure 8B:
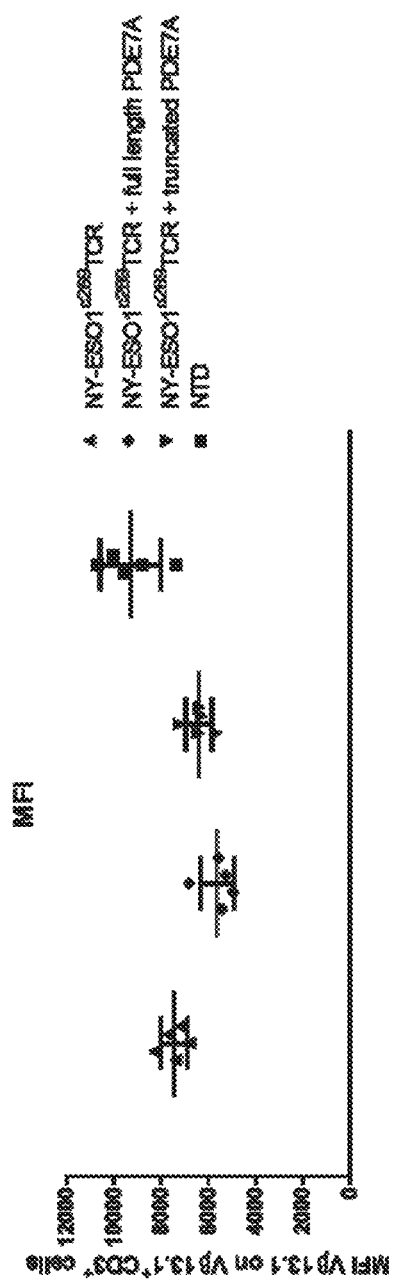

2.7 Transduction Efficiency and TCR Expression Level of T Cells Expressing NY-ESO1$^{c259}$ and Full-Length or Truncated Forms of PDE7A T cell transduction levels were determined by staining for the Vβ chain of the TCR (Vβ13.1). The amount of virus used for transduction was normalised after lentiviral titration leading to very similar transduction efficiencies for all constructs (FIG. 8A). The TCR expression level as measured by median fluorescence intensity (MFI) of Vβ13.1 was considerably lower for T cells transduced with NY-ESO1$^{c259}$ TCR+ full length PDE7A compared to T cells transduced with NY-ESO1$^{c259}$ TCR alone (FIG. 8B). T cells transduced with NY-ESO1$^{c259}$ TCR+ truncated PDE7A showed intermediate TCR expression levels.

2.8 Target Cell Killing Kinetics of T Cells Expressing NY-ESO1$^{c259}$ and Full-Length or Truncated Forms of PDE7A in the Presence of PGE2

The ability of T cells expressing (i) NY-ESO1$^{c259}$ TCR (ii) NY-ESO1$^{c259}$ TCR and full-length PDE7A or (iii) NY-ESO1$^{c259}$ TCR and truncated PDE7A to induce apoptosis of A375 target cells was measured by time-resolved cytotoxicity assay in the absence and presence of prostaglandin E2.

60,000 T cells with different transduction status were added to each assay well and co-incubated with HLA-A2+/NY-ESO+ A375 melanoma target cells seeded at 20,000 per well 24 hours prior to the assay. Prostaglandin E2 was added at a final concentration of 1 μM in each well. CellPlayer™ 96-Well Kinetic Caspase-3/7 reagent was added to all wells at a final concentration of 3.3 μM. Images were taken at intervals of 3 hours over a duration of 96 hours. The number of objects/mm$^2$, a measure of target cells undergoing apoptosis, was determined for each image and plotted against time.

Non-transduced T cells (NTD), T cells expressing NY-ESO1$^{c259}$ TCR, T cells expressing both NY-ESO1$^{c259}$ TCR and full-length PDE7A and T cells expressing both NY-ESO1$^{c259}$ TCR and truncated PDE7A were investigated for their ability to induce apoptosis of the target cells in the absence (closed symbols) or presence (open symbols) of PGE2 (FIG. 9A). The overexpression of both full-length and truncated PDE7A in NY-ESO specific T cells confers resistance to the inhibitory effects of PGE2 (FIG. 9C) although the effect was slightly reduced for the truncated PDE7A. T cells transduced with both forms of PDE7A showed killing kinetics with PGE2 present that were similar to that shown by the corresponding cells in the absence of PGE2 (FIG. 9B).

Data points show mean values and standard error to the mean of triplicate wells. FIG. 9 represents experiments performed with T cells isolated from one healthy donors. Data shown are representative of 4 experiments.

2.9 IFN-γ Secretion of T Cells Expressing NY-ESO1$^{c259}$ and Full-Length or Truncated Forms of PDE7A.

Sandwich ELISA was employed to investigate the effect of forskolin and PGE2 on IFN-γ secretion from T cells expressing NY-ESO1$^{c259}$ TCR, T cells expressing both NY-ESO1$^{c259}$ TCR and full-length PDE7A, and T cells expressing both NY-ESO1$^{c259}$ TCR and truncated PDE7A.

120,000 T cells isolated from a healthy donor transduced with lentivectors expressing the NY-ESO1-specific TCR c259 alone or in tandem with full-length phosphodiesterase 7A or truncated phosphodiesterase 7A were added to each assay well and co-incubated with HLA-A2+/NYESO+A375 melanoma cells seeded at 50,000 per well. Forskolin was added at a final concentration of 50 μM and prostaglandin E2 at 0.3 μM and 1 μM. T cells and target cells were co-cultured for 48 hours and the supernatants were collected for cytokine analysis.

Figure 10A:
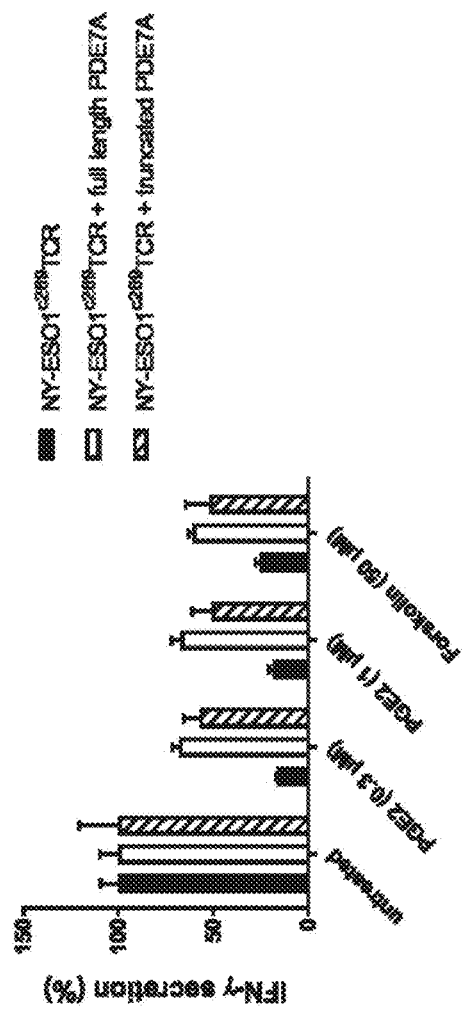
FIGS. 10A and 10B show that NY-ESO specific T cells overexpressing full-length or truncated PDE7A are partially resistant to the inhibition of cytokine release by mediators that increase intracellular cAMP.
Figure 10B:
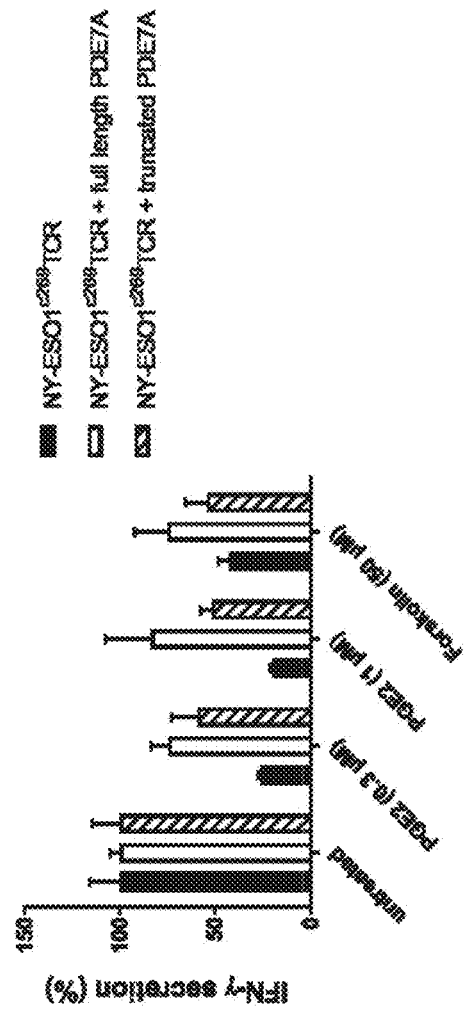

T cells expressing both forms of PDE7A showed resistance to the inhibitory effects of PGE2 and forskolin on IFN-γ release (FIG. 10). FIG. 10 represents experiments performed with T cells isolated from 2 healthy donors. Data shown are representative of 4 experiments.

Sequences

```
MEVCYQLPVLPLDRPVPQHVLSRRGAISFSSSSALFGCPNPRQLSQRRGAISYDSSDQTALYIRMLGDVRVR
SRAGFESERRGSHPYIDFRIFHSQSEIEVSVSARNIRRLLSFQRYLRSSRFFRGTAVSNSLNILDDDYNGQAKC
MLEKVGNWNFDIFLFDRLTNGNSLVSLTFHLFSLHGLIEYFHLDMMKLRRFLVMIQEDYHSQNPYHNAVH
AADVTQAMHCYLKEPKLANSVTPWDILLSLIAAATHDLDHPGVNQPFLIKTNHYLATLYKNTSVLENHHW
RSAVGLLRESGLFSHLPLESRQQMETQIGALILATDISRQNEYLSLFRSHLDRGDLCLEDTRHRHLVLQMAL
KCADICNPCRTWELSKQWSEKVTEEFFHQGDIEKKYHLGVSPLCDRHTESIANIQIGFMTYLVEPLFTEWAR
FSNTRLSQTMLGHVGLNKAS
WKGLQREQSSSEDTDAAFELNSQLLPQENRLS
SEQ ID NO: 1 (PDE7A) NP_001229247.1

MEPPTVPSERSLSLSLPGPREGQATLKPPPQHLWRQPRTPIRIQQRGYSDSAERAERERQPHRPIERADAMDT
SDRPGLRTTRMSWPSSFHGTGTGSGGAGGGSSRRFEAENGPTPSPGRSPLDSQASPGLVLHAGAATSQRRE
SFLYRSDSDYDMSPKTMSRNSSVTSEAHAEDLIVTPFAQVLASLRSVRSNFSLLTNVPVPSNKRSPLGGPTP
VCKATLSEETCQQLARETLEELDWCLEQLETMQTYRSVSEMASHKFKRMLNRELTHLSEMSRSGNQVSEY
ISTTFLDKQNEVEIPSPTMKEREKQQAPRPRPSQPPPPPVPHLQPMSQITGLKKLMHSNSLNNSNIPRFGVKT
DQEELLAQELENLNKWGLNIFCVSDYAGGRSLTCIMYMIFQERDLLKKFRIPVDTMVTYMLTLEDHYHAD
VAYHNSLHAADVLQSTHVLLA
TPALDAVFTDLEILAALFAAAIHDVDHPGVSNQFLINTNSELALMYNDESVLENHHLAVGFKLLQEDNCDIF
QNLSKRQRQSLRKMVIDMVLATDMSKHMTLLADLKTMVETKKVTSSGVLLLDNYSDRIQVLRNMVHCA
DLSNPTKPLELYRQWTDRIMAEFFQQGDRERERGMEISPMCDKHTASVEKSQVGFIDYIVHPLWETWADL
VHPDAQEILDTLEDNRDWYYSAIRQSPSPPPEEESRGPGHPPLPDKFQFELTLEEEEEEISMAQIPCTAQEAL
TAQGLSGVEEALDATIAWEASPAQESLEVMAQEASLEAELEAVYLTQQAQSTGSAPVAPDEFSSREEFVVA
VSHSSPSALALQSPLLPAWRTLSVSEHAPGLPGLPSTAAEVEAQREHQAAKRACSACAGTFGEDTSALPAP
GGGGSGGDPT
SEQ ID NO: 2 (PDE4A) NP_001104777.1

MENLGVGEGAEACSRLSRSRGRHSMTRAPKHLWRQPRRPIRIQQRFYSDPDKSAGCRERDLSPRPELRKSR
LSWPVSSCRRFDLENGLSCGRRALDPQSSPGLGRIMQAPVPHSQRRESFLYRSDSDYELSPKAMSRNSSVAS
DLHGEDMIVTPFAQVLASLRTVRSNVAALARQQCLGAAKQGPVGNPSSSNQLPPAEDTGQKLALETLDEL
DWCLDQLETLQTRHSVGEMASNKFKRILNRELTHLSETSRSGNQVSEYISRTFLDQQTEVELPKVTAEEAPQ
PMSRISGLHGLCHSASLSSATVPRFGVQTDQEEQLAKELEDTNKWGLDVFKVAELSGNRPLTAIIFSIFQERD
LLKTFQIPADTLATYLLMLEGHYHANVAYHNSLHAADVAQSTHVLLATPALEAVFTDLEILAALFASAIHD
VDHPGVSNQFLINTNSELALM
YNDASVLENHHLAVGFKLLQAENCDIFQNLSAKQRLSLRRMVIDMVLATDMSKHMNLLADLKTMVETKK
VTSLGVLLLDNYSDRIQVLQNLVHCADLSNPTKPLPLYRQWTDRIMAEFFQQGDRERESGLDISPMCDKHT
```

```
ASVEKSQVGFIDYIAHPLWETWADLVHPDAQDLLDTLEDNREWYQSKIPRSPSDLTNPERDGPDRFQFELT
LEEAEEEDEEEEEEGEETALAKEALELPDTELLSPEAGPDPGDLPLDNQRT
SEQ ID NO: 3 (PDE4C) NP_000914.2

MEVCYQLPVLPLDRPVPQHVLSRRGAISFSSSSALFGCPNPRQLSQRRGAISYDSSDQTALYIRMLGDVRV
RSRAGFESERRGSHPYIDFRIFHSQSEIEVSVSARNIRRLLSFQRYLRSSRFFRGTAVSNSLNILDDDYNGQAK
SEQ ID NO: 4 non-catalytic N terminal fragment of PDE7A (repeats are
underlined and PKA pseudosubtrate sites are in bold)

ATGGAAGTGTGCTACCAGCTGCCCGTGCTGCCCCTGGATAGACCTGTGCCTCAGCATGTGCTGAGCAG
AAGAGGCGCCATCAGCTTCAGCAGCAGCTCCGCCCTGTTCGGCTGCCCCAATCCTAGACAGCTGAGCC
AGAGAAGGGGAGCCATCTCCTACGACAGCAGCGACCAGACCGCCCTGTACATCAGAATGCTGGGCGA
CGTGCGCGTGCGGAGCAGAGCCGGATTTGAGAGCGAGAGAAGAGGCTCCCACCCCTACATCGACTTC
CGGATCTTCCACAGCCAGAGCGAGATCGAGGTGTCCGTGTCCGCCCGGAACATCAGACGGCTGCTGAG
CTTCCAGAGATACCTGAGAAGCAGCCGGTTCTTCCGGGGCACCGCCGTGTCCAACAGCCTGAACATCC
TGGACGACGACTACAACGGCCAGGCCAAGCGGGCCAAGAGATCTGGATCTGGCGCGCCGTGAAGCA
GACCCTGAACTTTGACCTGCTGAAACTGGCCGGCGACGTGGAAAGCAACCCTGGCCCCATGAAGAAG
CACCTGACCACCTTTCTCGTGATCCTGTGGCTGTACTTCTACCGGGGCAACGGCAAGAACCAGGTGGA
ACAGAGCCCCCAGAGCCTGATCATCCTGGAAGGCAAGAACTGCACTCTGCAGTGCAACTACACCGTGT
CCCCCTTCAGCAACCTGCGCTGGTACAAGCAGGATACCGGCAGAGGCCCTGTGTCCCTGACCATCCTG
ACCTTCAGCGAGAACACCAAGAGCAACGGCCGGTACACCGCCACCCTGGACGCCGATACAAAGCAGA
GCAGCCTGCACATCACCGCCTCCCAGCTGAGCGATAGCGCCAGCTACATCTGCGTGGTGTCCGGCGGC
ACAGACAGCTGGGGCAAGCTGCAGTTTGGCGCCGGAACACAGGTGGTCGTGACCCCCGACATCCAGA
ACCCTGACCCTGCCGTGTACCAGCTGCGGGACAGCAAGAGCAGCGACAAGAGCGTGTGCCTGTTCACC
GACTTCGACTCCCAGACCAACGTGTCCCAGAGCAAGGACAGCGACGTGTACATCACCGACAAGACCG
TGCTGGATATGCGGAGCATGGACTTCAAGAGCAATAGCGCCGTGGCCTGGTCTAACAAGAGCGACTTC
GCCTGCGCCAACGCCTTCAACAACAGCATTATCCCCGAGGACACATTCTTCCCAAGCCCCGAGAGCAG
CTGCGACGTGAAACTGGTGGAAAAGAGCTTCGAGACAGACACCAACCTGAATTTCCAGAACCTGAGC
GTGATCGGCTTCCGGATCCTGCTGCTGAAGGTGGCCGGATTCAACCTGCTGATGACCCTGCGGCTGTG
GTCCTCTGGCTCTCGGGCCAAGAGAAGCGGCAGCGGCGCCACCAATTTCAGCCTGCTGAAGCAGGCAG
GGGATGTGGAAGAGAATCCCGGCCCTAGAATGGCCTCCCTGCTGTTTTTCTGCGGCGCCTTCTACCTGC
TGGGGACCGGCAGCATGGACGCTGACGTGACCCAGACCCCCCGGAACAGAATCACCAAGACCGGCAA
GCGGATCATGCTGGAATGCAGCCAGACAAAGGGCCACGACCGGATGTACTGGTACAGACAGGATCCA
GGACTGGGCCTGAGGCTGATCTACTACAGCTTCGATGTGAAGGACATCAACAAGGGCGAGATCAGCG
ACGGCTACAGCGTGTCCAGACAGGCCCAGGCCAAGTTCTCCCTGAGCCTGGAAAGCGCCATCCCCAAC
CAGACCGCCCTGTACTTTTGTGCCACAAGCGGCCAGGGCGCCTACGAGGAACAGTTCTTTTGGCCCTGG
CACCCGGCTGACAGTGCTGGAAGATCTGAAGAACGTGTTCCCCCCAGAGGTGGCAGTGTTCGAGCCTA
GCGAGGCCGAGATCTCCCACACCCAGAAAGCCACACTCGTGTGTCTGGCCACCGGATTCTACCCCGAC
CATGTGGAACTGTCTTGGTGGGTCAACGGCAAAGAGGTGCACAGCGGCGTGTCCACCGATCCCCAGCC
TCTGAAAGAACAGCCCGCCCTGAACGACAGCCGGTACTGCCTGAGCAGCAGACTGAGAGTGCCGCC
ACCTTCTGGCAGAACCCCAGAAATCACTTCAGATGCCAGGTGCAGTTTTACGGCCTGAGCGAGAACGA
CGAGTGGACCCAGGATAGGGCCAAGCCCGTGACTCAGATCGTGTCTGCCGAAGCCTGGGGCAGAGCC
GATTGCGGCTTTACCAGCGAGAGCTACCAGCAGGGCGTGCTGAGCGCCACCATCCTGTACGAGATCCT
GCTGGGCAAGGCCACACTGTACGCCGTGCTGGTGTCTGCCCTGGTGCTGATGGCCATGGTCAAGCGGA
AGGACAGCCGGGGCTGA
SEQ ID NO: 5 coding sequence for truncated PDE7A with MAGE-A4 TCR MEVCYQLPVLPLDRPVPQHVLSRRGAISFSSSSALFGCPNPRQLSQRRGAISYDSSDQTALYIRMLGDVRVR
SRAGFESERRGSHPYIDFRIFHSQSEIEVSVSARNIRRLLSFQRYLRSSRFFRGTAVSNSLNILDDDYNGQAKR
AKRSGSGAPVKQTLNFDLLKLAGDVESNPGPMKKHLTTFLVILWLYFYRGNGKNQVEQSPQSLIILEGKNC
TLQCNYTVSPFSNLRWYKQDTGRGPVSLTILTFSENTKSNGRYTATLDADTKQSSLHITASQLSDSASYICV
VSGGTDSWGKLQFGAGTQVVVTPDIQNPDPAVYQLRDSKSSDKSVCLFTDFDSQTNVSQSKDSDVYITDK
TVLDMRSMDFKSNSAVAWSNKSDFACANAFNNSIIPEDTFFPSPESSCDVKLVEKSFETDTNLNFQNLSVIG
FRILLLKVAGFNLLMTLRLWSSGSRAKRSGSGATNFSLLKQAGDVEENPGPRMASLLFFCGAFYLLGTGSM
DADVTQTPRNRITKTGKRIMLECSQTKGHDRMYWYRQDPGLGLRLIYYSFDVKDINKGEISDGYSVSRQA
QAKFSLSLESAIPNQTALYFCATSGQGAYEEQFFGPGTRLTVLEDLKNVFPPEVAVFEPSEAEISHTQKATLV
CLATGFYPDHVELSWWVNGKEVHSGVSTDPQPLKEQPALNDSRYCLSSRLRVSATFWQNPRNHFRCQVQF
YGLSENDEWTQDRAKPVTQIVSAEAWGRADCGFTSESYQQGVLSATILYEILLGKATLYAVLVSALVLMA
MVKRKDSRG*
SEQ ID NO: 6 amino acid sequence for truncated PDE7A (underlined) with MAGE-A4 TCR ATGGAAGTGTGCTACCAGCTGCCCGTGCTGCCCCTGGATAGACCTGTGCCTCAGCATGTGCTGAGCAG
AAGAGGCGCCATCAGCTTCAGCAGCAGCTCCGCCCTGTTCGGCTGCCCCAATCCTAGACAGCTGAGCC
AGAGAAGGGGAGCCATCTCCTACGACAGCAGCGACCAGACCGCCCTGTACATCAGAATGCTGGGCGA
CGTGCGCGTGCGGAGCAGAGCCGGATTTGAGAGCGAGAGAAGAGGCTCCCACCCCTACATCGACTTC
CGGATCTTCCACAGCCAGAGCGAGATCGAGGTGTCCGTGTCCGCCCGGAACATCAGACGGCTGCTGAG
CTTCCAGAGATACCTGAGAAGCAGCCGGTTCTTCCGGGGCACCGCCGTGTCCAACAGCCTGAACATCC
TGGACGACGACTACAACGGCCAGGCCAAGCGGGCCAAGAGATCTGGAAGCGGAGCCCCTGTGAAGCA
GACCCTGAACTTCGATCTGCTGAAACTGGCCGGCGACGTGGAAAGCAACCCTGGCCCCATGAAACAC
TGCTGGGACTGCTGATCCTGTGGCTGCAGCTGCAGTGGGTGTCCAGCAAGCAGGAGGTGACCCAGATC
CCTGCCGCCCTGAGCGTGCCCGAGGGCGAGAACCTGGTGCTGAACTGCAGCTTCACCGACTCTGCCAT
CTACAACCTGCAGTGGTTCCGGCAGGACCCCGGCAAGGGCCTGACCAGCCTGCTGCTGATCCAGAGCA
GCCAGCGGGAGCAGACCAGCGGACGGCTGAACGCCAGCCTGGACAAGAGCAGCGGCCGGAGCACCCT
GTACATCGCCGCCAGCCAGCCCGGCGACAGCGCCACCTACCTGTGCGCTGTGCGGCCTCTGTACGGCG
GCAGCTACATCCCCACCTTCGGCAGAGGCACCAGCCTGATCGTGCACCCCTACATCCAGAACCCCGAC
CCCGCCGTGTACCAGCTGCGGGACAGCAAGAGCAGCGACAAGTCTGTGTGCCTGTTCACCGACTTCGA
CAGCCAGACCAATGTGAGCCAGAGCAAGGACAGCGACGTGTACATCACCGACAAGACCGTGCTGGAC
```

| Sequences |
|---|
| ATGCGGAGCATGGACTTCAAGAGCAACAGCGCCGTGGCCTGGAGCAACAAGAGCGACTTCGCCTGCG<br>CCAACGCCTTCAACAACAGCATTATCCCCGAGGACACCTTCTTCCCCAGCCCCGAGAGCAGCTGCGAC<br>GTGAAACTGGTGGAGAAGAGCTTCGAGACCGACACCAACCTGAACTTCCAGAACCTGAGCGTGATCG<br>GCTTCAGAATCCTGCTGCTGAAGGTGGCCGGATTCAACCTGCTGATGACCCTGCGGCTGTGGAGCAGC<br>GGCTCCCGGGCAAGAGAAGCGGATCCGGCGCCACCAACTTCAGCCTGCTGAAGCAGGCCGGAGACG<br>TGGAAGAAAACCCTGGCCCTAGGATGAGCATCGGCCTGCTGTGCTGCGCCGCCCTGAGCCTGCTGTGG<br>GCAGGACCCGTGAACGCCGGAGTGACCCAGACCCCCAAGTTCCAGGTGCTGAAAACCGGCCAGAGCA<br>TGACCCTGCAGTGCGCCCAGGACATGAACCACGAGTACATGAGCTGGTATCGGCAGGACCCCGGCAT<br>GGGCCTGCGGCTGATCCACTACTCTGTGGGAGCCGGAATCACCGACCAGGGCGAGGTGCCCAACGGCT<br>ACAATGTGAGCCGGAGCACCACCGAGGACTTCCCCCTGCGGCTGCTGAGCGCTGCCCCCAGCCAGACC<br>AGCGTGTACTTCTGCGCCAGCAGCTATGTGGGCAACACCGGCGAGCTGTTCTTCGGCGAGGGCTCCAG<br>GCTGACCGTGCTGGAGGACCTGAAGAACGTGTTCCCCCCCGAGGTGGCCGTGTTCGAGCCCAGCGAGG<br>CCGAGATCAGCCACACCCAGAAGGCCACACTGGTGTGTCTGGCCACCGGCTTCTACCCCGACCACGTG<br>GAGCTGTCCTGGTGGGTGAACGGCAAGGAGGTGCACAGCGGCGTGTCTACCGACCCCCAGCCCCTGA<br>AGGAGCAGCCCGCCCTGAACGACAGCCGGTACTGCCTGTCCTCCAGACTGAGAGTGAGCGCCACCTTC<br>TGGCAGAACCCCCGGAACCACTTCCGGTGCCAGGTGCAGTTCTACGGCCTGAGCGAGAACGACGAGT<br>GGACCCAGGACCGGGCCAAGCCCGTGACCCAGATTGTGAGCGCCGAGGCCTGGGGCAGGGCCGACTG<br>CGGCTTCACCAGCGAGAGCTACCAGCAGGGCGTGCTGAGCGCCACCATCCTGTACGAGATCCTGCTGG<br>GCAAGGCCACCCTGTACGCCGTGCTGGTGTCTGCCCTGGTGCTGATGGCTATGGTGAAGCGGAAGGAC<br>AGCCGGGGCTAA<br>SEQ ID NO: 7 coding sequence for truncated PDE7A with NY-ESO TCR |
| <u>MEVCYQLPVLPLDRPVPQHVLSRRGAISFSSSSALFGCPNPRQLSQRRGAISYDSSDQTALYIRMLGDVRVR<br>SRAGFESERRGSHPYIDFRIFHSQSEIEVSVSARNIRRLLSFQRYLRSSRFFRGTAVSNSLNILDDDYNGQAKR</u><br>AKRSGSGAPVKQTLNFDLLKLAGDVESNPGPMETLLGLLILWLQLQWVSSKQEVTQIPAALSVPEGENLVL<br>NCSFTDSAIYNLQWFRDPGKGLTSLLLIQSSQREQTSGRLNASLDKSSGRSTLYIAASQPGDSATYLCAVR<br>PLYGGSYIPTFGRGTSLIVHPYIQNPDDPAVYQLRDSKSSDKSVCLFTDFDSQTNVSQSKDSDVYITDKTVLD<br>MRSMDFKSNSAVAWSNKSDFACANAFNNSIIPEDTFFPSPESSCDVKLVEKSFETDTNLNFQNLSVIGFRILL<br>LKVAGFNLLMTLRLWSSGSRAKRSGSGATNFSLLKQAGDVEENPGPRMSIGLLCCAALSLLWAGPVNAGV<br>TQTPKFQVLKTGQSMTLQCAQDMNHEYMSWYRQDPGMGLRLIHYSVGAGITDQGEVPNGYNVSRSTTED<br>FPLRLLSAAPSQTSVYFCASSYVGNTGELFFGEGSRLTVLEDLKNVFPPEVAVFEPSEAEISHTQKATLVCLA<br>TGFYPDHVELSWWVNGKEVHSGVSTDPQPLKEQPALNDSRYCLSSRLRVSATFWQNPRNHFRCQVQFYG<br>LSENDEWTQDRAKPVTQIVSAEAWGRADCGFTSESYQQGVLSATILYEILLGKATLYAVLVSALVLMAMV<br>KRKDSRG*<br>SEQ ID NO: 8 amino acid sequence for truncated PDE7A (underlined) with NY-ESO TCR |

What is claimed is:

1. A population of modified T cells which express an antigen receptor which binds specifically to cancer cells and a cAMP phosphodiesterase (PDE) or fragment thereof, wherein said cells comprise a heterologous nucleic acid encoding the cAMP phosphodiesterase (PDE).

2. The population of claim 1 wherein the nucleic acid encoding the cAMP PDE or fragment is comprised in an expression vector.

3. The population of claim 1 wherein the cAMP phosphodiesterase (PDE) is cAMP phosphodiesterase 7A (PDE7A) or cAMP phosphodiesterase 4C (PDE4C).

4. The population of claim 1 wherein the antigen receptor is a T cell receptor (TCR).

5. The population of claim 4 wherein the antigen receptor is a heterologous TCR.

6. The population of claim 5 wherein said cells comprise a heterologous nucleic acid encoding the TCR.

7. The population of claim 6 wherein the heterologous nucleic acid encoding the TCR is comprised in an expression vector.

8. The population of claim 4 wherein the TCR binds specifically to an MHC displaying a peptide fragment of a tumour antigen expressed by the cancer cells.

9. The population of claim 8 wherein the tumour antigen is NY-ESO-1, MAGE-A4 or MAGE-A10.

10. The population of claim 1 wherein the antigen receptor is a chimeric antigen receptor (CAR).

11. The population of claim 10 wherein the CAR binds specifically to a tumour antigen expressed by the cancer cells.

12. The population of claim 1 wherein the cancer cells are melanoma cells.

13. The population of claim 1 wherein the population of modified T cells comprises CD4$^+$ T cells; CD8$^+$ T cells; or CD4$^+$ T cells and CD8$^+$ T cells.

14. The population of claim 1 wherein the modified T cells are produced by a method comprising modifying a population of T cells obtained from a donor individual to express a cAMP phosphodiesterase (PDE) or a fragment thereof.

15. The population of claim 14 wherein the T cells express an antigen receptor which binds specifically to cancer cells from the donor individual.

16. The population of claim 14 wherein the method further comprises modifying the population of T cells to express an antigen receptor which binds specifically to cancer cells.

17. A pharmaceutical composition comprising the population of claim 1 and a pharmaceutically acceptable excipient.

* * * * *

SEQUENCE LISTING

<160> NUMBER OF SEQ ID NOS: 40

<210> SEQ ID NO 1
<211> LENGTH: 482
<212> TYPE: PRT
<213> ORGANISM: Artificial Sequence
<220> FEATURE:
<223> OTHER INFORMATION: (PDE7A) NP_001229247.1

<400> SEQUENCE: 1

Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Asp Tyr Asn Gly Gln Ala
    130                 135                 140

Lys Cys Met Leu Glu Lys Val Gly Asn Trp Asn Phe Asp Ile Phe Leu
145                 150                 155                 160

Phe Asp Arg Leu Thr Asn Gly Asn Ser Leu Val Ser Leu Thr Phe His
                165                 170                 175

Leu Phe Ser Leu His Gly Leu Ile Glu Tyr Phe His Leu Asp Met Met
            180                 185                 190

Lys Leu Arg Arg Phe Leu Val Met Ile Gln Glu Asp Tyr His Ser Gln
        195                 200                 205

Asn Pro Tyr His Asn Ala Val His Ala Ala Asp Val Thr Gln Ala Met
210                 215                 220

His Cys Tyr Leu Lys Glu Pro Lys Leu Ala Asn Ser Val Thr Pro Trp
225                 230                 235                 240

Asp Ile Leu Leu Ser Leu Ile Ala Ala Ala Thr His Asp Leu Asp His
                245                 250                 255

Pro Gly Val Asn Gln Pro Phe Leu Ile Lys Thr Asn His Tyr Leu Ala
            260                 265                 270

Thr Leu Tyr Lys Asn Thr Ser Val Leu Glu Asn His His Trp Arg Ser
        275                 280                 285

Ala Val Gly Leu Leu Arg Glu Ser Gly Leu Phe Ser His Leu Pro Leu
290                 295                 300

Glu Ser Arg Gln Gln Met Glu Thr Gln Ile Gly Ala Leu Ile Leu Ala
305                 310                 315                 320

Thr Asp Ile Ser Arg Gln Asn Glu Tyr Leu Ser Leu Phe Arg Ser His
                325                 330                 335

Leu Asp Arg Gly Asp Leu Cys Leu Glu Asp Thr Arg His Arg His Leu
            340                 345                 350

Val Leu Gln Met Ala Leu Lys Cys Ala Asp Ile Cys Asn Pro Cys Arg
        355                 360                 365

Thr Trp Glu Leu Ser Lys Gln Trp Ser Glu Lys Val Thr Glu Glu Phe
370                 375                 380

Phe His Gln Gly Asp Ile Glu Lys Lys Tyr His Leu Gly Val Ser Pro
385                 390                 395                 400

Leu Cys Asp Arg His Thr Glu Ser Ile Ala Asn Ile Gln Ile Gly Phe
                405                 410                 415

Met Thr Tyr Leu Val Glu Pro Leu Phe Thr Glu Trp Ala Arg Phe Ser
            420                 425                 430

Asn Thr Arg Leu Ser Gln Thr Met Leu Gly His Val Gly Leu Asn Lys
        435                 440                 445

Ala Ser Trp Lys Gly Leu Gln Arg Glu Gln Ser Ser Ser Glu Asp Thr
450                 455                 460

Asp Ala Ala Phe Glu Leu Asn Ser Gln Leu Leu Pro Gln Glu Asn Arg
465                 470                 475                 480

Leu Ser

<210> SEQ ID NO 2
<211> LENGTH: 886
<212> TYPE: PRT
<213> ORGANISM: Artificial Sequence
<220> FEATURE:
<223> OTHER INFORMATION: (PDE4A) NP_001104777.1

<400> SEQUENCE: 2

Met Glu Pro Pro Thr Val Pro Ser Glu Arg Ser Leu Ser Leu Ser Leu

```
1               5                   10                  15
Pro Gly Pro Arg Glu Gly Gln Ala Thr Leu Lys Pro Pro Gln His
            20                  25                  30
Leu Trp Arg Gln Pro Arg Thr Pro Ile Arg Ile Gln Gln Arg Gly Tyr
            35                  40                  45
Ser Asp Ser Ala Glu Arg Ala Glu Arg Glu Arg Gln Pro His Arg Pro
            50                  55                  60
Ile Glu Arg Ala Asp Ala Met Asp Thr Ser Asp Arg Pro Gly Leu Arg
65                  70                  75                  80
Thr Thr Arg Met Ser Trp Pro Ser Ser Phe His Gly Thr Gly Thr Gly
                85                  90                  95
Ser Gly Gly Ala Gly Gly Ser Ser Arg Arg Phe Glu Ala Glu Asn
                100                 105                 110
Gly Pro Thr Pro Ser Pro Gly Arg Ser Pro Leu Asp Ser Gln Ala Ser
            115                 120                 125
Pro Gly Leu Val Leu His Ala Gly Ala Ala Thr Ser Gln Arg Arg Glu
            130                 135                 140
Ser Phe Leu Tyr Arg Ser Asp Ser Asp Tyr Asp Met Ser Pro Lys Thr
145                 150                 155                 160
Met Ser Arg Asn Ser Ser Val Thr Ser Glu Ala His Ala Glu Asp Leu
                165                 170                 175
Ile Val Thr Pro Phe Ala Gln Val Leu Ala Ser Leu Arg Ser Val Arg
                180                 185                 190
Ser Asn Phe Ser Leu Leu Thr Asn Val Pro Val Pro Ser Asn Lys Arg
                195                 200                 205
Ser Pro Leu Gly Gly Pro Thr Pro Val Cys Lys Ala Thr Leu Ser Glu
            210                 215                 220
Glu Thr Cys Gln Gln Leu Ala Arg Glu Thr Leu Glu Glu Leu Asp Trp
225                 230                 235                 240
Cys Leu Glu Gln Leu Glu Thr Met Gln Thr Tyr Arg Ser Val Ser Glu
                245                 250                 255
Met Ala Ser His Lys Phe Lys Arg Met Leu Asn Arg Glu Leu Thr His
                260                 265                 270
Leu Ser Glu Met Ser Arg Ser Gly Asn Gln Val Ser Glu Tyr Ile Ser
            275                 280                 285
Thr Thr Phe Leu Asp Lys Gln Asn Glu Val Glu Ile Pro Ser Pro Thr
            290                 295                 300
Met Lys Glu Arg Glu Lys Gln Gln Ala Pro Arg Pro Arg Pro Ser Gln
305                 310                 315                 320
Pro Pro Pro Pro Pro Val Pro His Leu Gln Pro Met Ser Gln Ile Thr
                325                 330                 335
Gly Leu Lys Lys Leu Met His Ser Asn Ser Leu Asn Asn Ser Asn Ile
            340                 345                 350
Pro Arg Phe Gly Val Lys Thr Asp Gln Glu Glu Leu Leu Ala Gln Glu
            355                 360                 365
Leu Glu Asn Leu Asn Lys Trp Gly Leu Asn Ile Phe Cys Val Ser Asp
            370                 375                 380
Tyr Ala Gly Gly Arg Ser Leu Thr Cys Ile Met Tyr Met Ile Phe Gln
385                 390                 395                 400
Glu Arg Asp Leu Leu Lys Lys Phe Arg Ile Pro Val Asp Thr Met Val
                405                 410                 415
Thr Tyr Met Leu Thr Leu Glu Asp His Tyr His Ala Asp Val Ala Tyr
                420                 425                 430
```

```
His Asn Ser Leu His Ala Ala Asp Val Leu Gln Ser Thr His Val Leu
        435                 440                 445

Leu Ala Thr Pro Ala Leu Asp Ala Val Phe Thr Asp Leu Glu Ile Leu
450                 455                 460

Ala Ala Leu Phe Ala Ala Ile His Asp Val Asp His Pro Gly Val
465                 470                 475                 480

Ser Asn Gln Phe Leu Ile Asn Thr Asn Ser Glu Leu Ala Leu Met Tyr
            485                 490                 495

Asn Asp Glu Ser Val Leu Glu Asn His His Leu Ala Val Gly Phe Lys
                500                 505                 510

Leu Leu Gln Glu Asp Asn Cys Asp Ile Phe Gln Asn Leu Ser Lys Arg
            515                 520                 525

Gln Arg Gln Ser Leu Arg Lys Met Val Ile Asp Met Val Leu Ala Thr
            530                 535                 540

Asp Met Ser Lys His Met Thr Leu Leu Ala Asp Leu Lys Thr Met Val
545                 550                 555                 560

Glu Thr Lys Lys Val Thr Ser Ser Gly Val Leu Leu Leu Asp Asn Tyr
                565                 570                 575

Ser Asp Arg Ile Gln Val Leu Arg Asn Met Val His Cys Ala Asp Leu
            580                 585                 590

Ser Asn Pro Thr Lys Pro Leu Glu Leu Tyr Arg Gln Trp Thr Asp Arg
            595                 600                 605

Ile Met Ala Glu Phe Phe Gln Gln Gly Asp Arg Glu Arg Glu Arg Gly
610                 615                 620

Met Glu Ile Ser Pro Met Cys Asp Lys His Thr Ala Ser Val Glu Lys
625                 630                 635                 640

Ser Gln Val Gly Phe Ile Asp Tyr Ile Val His Pro Leu Trp Glu Thr
            645                 650                 655

Trp Ala Asp Leu Val His Pro Asp Ala Gln Glu Ile Leu Asp Thr Leu
            660                 665                 670

Glu Asp Asn Arg Asp Trp Tyr Tyr Ser Ala Ile Arg Gln Ser Pro Ser
            675                 680                 685

Pro Pro Pro Glu Glu Ser Arg Gly Pro Gly His Pro Pro Leu Pro
            690                 695                 700

Asp Lys Phe Gln Phe Glu Leu Thr Leu Glu Glu Glu Glu Glu Glu
705                 710                 715                 720

Ile Ser Met Ala Gln Ile Pro Cys Thr Ala Gln Glu Ala Leu Thr Ala
            725                 730                 735

Gln Gly Leu Ser Gly Val Glu Glu Ala Leu Asp Ala Thr Ile Ala Trp
            740                 745                 750

Glu Ala Ser Pro Ala Gln Glu Ser Leu Glu Val Met Ala Gln Glu Ala
            755                 760                 765

Ser Leu Glu Ala Glu Leu Glu Ala Val Tyr Leu Thr Gln Gln Ala Gln
            770                 775                 780

Ser Thr Gly Ser Ala Pro Val Ala Pro Asp Glu Phe Ser Ser Arg Glu
785                 790                 795                 800

Glu Phe Val Val Ala Val Ser His Ser Ser Pro Ser Ala Leu Ala Leu
                805                 810                 815

Gln Ser Pro Leu Leu Pro Ala Trp Arg Thr Leu Ser Val Ser Glu His
            820                 825                 830

Ala Pro Gly Leu Pro Gly Leu Pro Ser Thr Ala Ala Glu Val Glu Ala
            835                 840                 845
```

Gln Arg Glu His Gln Ala Ala Lys Arg Ala Cys Ser Ala Cys Ala Gly
            850                 855                 860

Thr Phe Gly Glu Asp Thr Ser Ala Leu Pro Ala Pro Gly Gly Gly Gly
865                 870                 875                 880

Ser Gly Gly Asp Pro Thr
                885

<210> SEQ ID NO 3
<211> LENGTH: 712
<212> TYPE: PRT
<213> ORGANISM: Artificial Sequence
<220> FEATURE:
<223> OTHER INFORMATION: (PDE4C) NP_000914.2

<400> SEQUENCE: 3

Met Glu Asn Leu Gly Val Gly Glu Gly Ala Glu Ala Cys Ser Arg Leu
1               5                   10                  15

Ser Arg Ser Arg Gly Arg His Ser Met Thr Arg Ala Pro Lys His Leu
            20                  25                  30

Trp Arg Gln Pro Arg Arg Pro Ile Arg Ile Gln Gln Arg Phe Tyr Ser
        35                  40                  45

Asp Pro Asp Lys Ser Ala Gly Cys Arg Glu Arg Asp Leu Ser Pro Arg
    50                  55                  60

Pro Glu Leu Arg Lys Ser Arg Leu Ser Trp Pro Val Ser Ser Cys Arg
65                  70                  75                  80

Arg Phe Asp Leu Glu Asn Gly Leu Ser Cys Gly Arg Arg Ala Leu Asp
                85                  90                  95

Pro Gln Ser Ser Pro Gly Leu Gly Arg Ile Met Gln Ala Pro Val Pro
            100                 105                 110

His Ser Gln Arg Arg Glu Ser Phe Leu Tyr Arg Ser Asp Ser Asp Tyr
        115                 120                 125

Glu Leu Ser Pro Lys Ala Met Ser Arg Asn Ser Ser Val Ala Ser Asp
    130                 135                 140

Leu His Gly Glu Asp Met Ile Val Thr Pro Phe Ala Gln Val Leu Ala
145                 150                 155                 160

Ser Leu Arg Thr Val Arg Ser Asn Val Ala Ala Leu Ala Arg Gln Gln
                165                 170                 175

Cys Leu Gly Ala Ala Lys Gln Gly Pro Val Gly Asn Pro Ser Ser Ser
            180                 185                 190

Asn Gln Leu Pro Pro Ala Glu Asp Thr Gly Gln Lys Leu Ala Leu Glu
        195                 200                 205

Thr Leu Asp Glu Leu Asp Trp Cys Leu Asp Gln Leu Glu Thr Leu Gln
    210                 215                 220

Thr Arg His Ser Val Gly Glu Met Ala Ser Asn Lys Phe Lys Arg Ile
225                 230                 235                 240

Leu Asn Arg Glu Leu Thr His Leu Ser Glu Thr Ser Arg Ser Gly Asn
                245                 250                 255

Gln Val Ser Glu Tyr Ile Ser Arg Thr Phe Leu Asp Gln Gln Thr Glu
            260                 265                 270

Val Glu Leu Pro Lys Val Thr Ala Glu Glu Ala Pro Gln Pro Met Ser
        275                 280                 285

Arg Ile Ser Gly Leu His Gly Leu Cys His Ser Ala Ser Leu Ser Ser
    290                 295                 300

Ala Thr Val Pro Arg Phe Gly Val Gln Thr Asp Gln Glu Glu Gln Leu
305                 310                 315                 320

Ala Lys Glu Leu Glu Asp Thr Asn Lys Trp Gly Leu Asp Val Phe Lys
            325                 330                 335

Val Ala Glu Leu Ser Gly Asn Arg Pro Leu Thr Ala Ile Ile Phe Ser
        340                 345                 350

Ile Phe Gln Glu Arg Asp Leu Leu Lys Thr Phe Gln Ile Pro Ala Asp
            355                 360                 365

Thr Leu Ala Thr Tyr Leu Leu Met Leu Glu Gly His Tyr His Ala Asn
        370                 375                 380

Val Ala Tyr His Asn Ser Leu His Ala Ala Asp Val Ala Gln Ser Thr
385                 390                 395                 400

His Val Leu Leu Ala Thr Pro Ala Leu Glu Ala Val Phe Thr Asp Leu
            405                 410                 415

Glu Ile Leu Ala Ala Leu Phe Ala Ser Ala Ile His Asp Val Asp His
            420                 425                 430

Pro Gly Val Ser Asn Gln Phe Leu Ile Asn Thr Asn Ser Glu Leu Ala
        435                 440                 445

Leu Met Tyr Asn Asp Ala Ser Val Leu Glu Asn His His Leu Ala Val
    450                 455                 460

Gly Phe Lys Leu Leu Gln Ala Glu Asn Cys Asp Ile Phe Gln Asn Leu
465                 470                 475                 480

Ser Ala Lys Gln Arg Leu Ser Leu Arg Arg Met Val Ile Asp Met Val
            485                 490                 495

Leu Ala Thr Asp Met Ser Lys His Met Asn Leu Leu Ala Asp Leu Lys
        500                 505                 510

Thr Met Val Glu Thr Lys Lys Val Thr Ser Leu Gly Val Leu Leu Leu
    515                 520                 525

Asp Asn Tyr Ser Asp Arg Ile Gln Val Leu Gln Asn Leu Val His Cys
530                 535                 540

Ala Asp Leu Ser Asn Pro Thr Lys Pro Leu Pro Leu Tyr Arg Gln Trp
545                 550                 555                 560

Thr Asp Arg Ile Met Ala Glu Phe Phe Gln Gln Gly Asp Arg Glu Arg
            565                 570                 575

Glu Ser Gly Leu Asp Ile Ser Pro Met Cys Asp Lys His Thr Ala Ser
        580                 585                 590

Val Glu Lys Ser Gln Val Gly Phe Ile Asp Tyr Ile Ala His Pro Leu
    595                 600                 605

Trp Glu Thr Trp Ala Asp Leu Val His Pro Asp Ala Gln Asp Leu Leu
        610                 615                 620

Asp Thr Leu Glu Asp Asn Arg Glu Trp Tyr Gln Ser Lys Ile Pro Arg
625                 630                 635                 640

Ser Pro Ser Asp Leu Thr Asn Pro Glu Arg Asp Gly Pro Asp Arg Phe
            645                 650                 655

Gln Phe Glu Leu Thr Leu Glu Glu Ala Glu Glu Asp Glu Glu Glu
        660                 665                 670

Glu Glu Glu Gly Glu Glu Thr Ala Leu Ala Lys Glu Ala Leu Glu Leu
    675                 680                 685

Pro Asp Thr Glu Leu Leu Ser Pro Glu Ala Gly Pro Asp Pro Gly Asp
690                 695                 700

Leu Pro Leu Asp Asn Gln Arg Thr
705                 710

<210> SEQ ID NO 4
<211> LENGTH: 145
<212> TYPE: PRT

<213> ORGANISM: Artificial Sequence
<220> FEATURE:
<223> OTHER INFORMATION: non-catalytic N terminal fragment of PDE7A

<400> SEQUENCE: 4

```
Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Asp Tyr Asn Gly Gln Ala
    130                 135                 140

Lys
145
```

<210> SEQ ID NO 5
<211> LENGTH: 2385
<212> TYPE: DNA
<213> ORGANISM: Artificial Sequence
<220> FEATURE:
<223> OTHER INFORMATION: coding sequence for truncated PDE7A with MAGE-A4 TCR

<400> SEQUENCE: 5

```
atggaagtgt gctaccagct gcccgtgctg cccctggata gacctgtgcc tcagcatgtg    60
ctgagcagaa gaggcgccat cagcttcagc agcagctccg ccctgttcgg ctgccccaat   120
cctagacagc tgagccagag aaggggagcc atctcctacg acagcagcga ccagaccgcc   180
ctgtacatca gaatgctggg cgacgtgcgc gtgcggagca gagccggatt tgagagcgag   240
agaagaggct cccaccccta catcgacttc cggatcttcc acagccagag cgagatcgag   300
gtgtccgtgt ccgcccggaa catcagacgg ctgctgagct tccagagata cctgagaagc   360
agccggttct tccggggcac cgccgtgtcc aacagcctga acatcctgga cgacgactac   420
aacggccagg ccaagcgggc caagagatct ggatctggcg cgcccgtgaa gcagaccctg   480
aactttgacc tgctgaaact ggccggcgac gtggaaagca ccctggcccc catgaagaag   540
cacctgacca ccttttctcgt gatcctgtgg ctgtacttct accggggcaa cggcaagaac   600
caggtggaac agagccccca gagcctgatc atcctggaag gcaagaactg cactctgcag   660
tgcaactaca ccgtgtcccc cttcagcaac ctgcgctggt acaagcagga taccggcaga   720
ggccctgtgt ccctgaccat cctgacc ttc agcgagaaca ccaagagcaa cggccggtac   780
accgccaccc tggacgccga tacaaagcag agcagcctgc acatcaccgc ctcccagctg   840
agcgatagcg ccagctacat ctgcgtggtg tccggcggca cagacagctg ggcaagctg   900 cagtttggcg ccggaacaca ggtggtcgtg acccccgaca tccagaaccc tgaccctgcc   960
```

```
gtgtaccagc tgcgggacag caagagcagc gacaagagcg tgtgcctgtt caccgacttc    1020
gactcccaga ccaacgtgtc ccagagcaag gacagcgacg tgtacatcac cgacaagacc    1080
gtgctggata tgcggagcat ggacttcaag agcaatagcg ccgtggcctg gtctaacaag    1140
agcgacttcg cctgcgccaa cgccttcaac aacagcatta tccccgagga cacattcttc    1200
ccaagccccg agagcagctg cgacgtgaaa ctggtggaaa gagcttcga cagacacc      1260 aacctgaatt ccagaacct gagcgtgatc ggcttccga tcctgctgct gaaggtggcc    1320
ggattcaacc tgctgatgac cctgcggctg tggtcctctg gctctcgggc aagagaagc    1380 ggcagcggcg ccaccaattt cagcctgctg aagcaggcag gggatgtgga agagaatccc    1440
ggccctagaa tggcctccct gctgttttc tgcggcgcct tctacctgct ggggaccggc    1500
agcatggacg ctgacgtgac ccagacccc cggaacagaa tcaccaagac cggcaagcgg    1560
atcatgctgg aatgcagcca gacaaagggc cacgaccgga tgtactggta cagacaggat    1620
ccaggactgg gcctgaggct gatctactac agcttcgatg tgaaggacat caacaagggc    1680
gagatcagcg acggctacag cgtgtccaga caggcccagg ccaagttctc cctgagcctg    1740
gaaagcgcca tccccaacca gaccgccctg tacttttgtg ccacaagcgg ccagggcgcc    1800
tacgaggaac agttctttgg ccctggcacc cggctgacga tgctggaaga tctgaagaac    1860
gtgttccccc cagaggtggc agtgttcgag cctagcgagg ccgagatctc ccacacccag    1920
aaagccacac tcgtgtgtct ggccaccgga ttctaccccg accatgtgga actgtcttgg    1980
tgggtcaacg gcaaagaggt gcacagcggc gtgtccaccg atccccagcc tctgaaagaa    2040
cagcccgccc tgaacgacag ccggtactgc ctgagcagca gactgagagt gtccgccacc    2100
ttctggcaga accccagaaa tcacttcaga tgccaggtgc agttttacgg cctgagcgag    2160
aacgacgagt ggacccagga tagggccaag cccgtgactc agatcgtgtc tgccgaagcc    2220
tggggcagag ccgattgcgg ctttaccagc gagagctacc agcagggcgt gctgagcgcc    2280
accatcctgt acgagatcct gctgggcaag gccacactgt acgccgtgct ggtgtctgcc    2340
ctggtgctga tggccatggt caagcggaag gacagccggg gctga                   2385
```

<210> SEQ ID NO 6
<211> LENGTH: 794
<212> TYPE: PRT
<213> ORGANISM: Artificial Sequence
<220> FEATURE:
<223> OTHER INFORMATION: amino acid sequence for truncated PDE7A with MAGE-A4 TCR

<400> SEQUENCE: 6

```
Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110
```

```
Ser Phe Gln Arg Tyr Leu Arg Ser Arg Phe Phe Arg Gly Thr Ala
    115                 120                 125

Val Ser Asn Ser Leu Asn Ile Leu Asp Asp Asp Tyr Asn Gly Gln Ala
130             135                 140

Lys Arg Ala Lys Arg Ser Gly Ser Gly Ala Pro Val Lys Gln Thr Leu
145             150                 155                 160

Asn Phe Asp Leu Leu Lys Leu Ala Gly Asp Val Glu Ser Asn Pro Gly
                165                 170                 175

Pro Met Lys Lys His Leu Thr Thr Phe Leu Val Ile Leu Trp Leu Tyr
            180                 185                 190

Phe Tyr Arg Gly Asn Gly Lys Asn Gln Val Glu Gln Ser Pro Gln Ser
        195                 200                 205

Leu Ile Ile Leu Glu Gly Lys Asn Cys Thr Leu Gln Cys Asn Tyr Thr
    210                 215                 220

Val Ser Pro Phe Ser Asn Leu Arg Trp Tyr Lys Gln Asp Thr Gly Arg
225             230                 235                 240

Gly Pro Val Ser Leu Thr Ile Leu Thr Phe Ser Glu Asn Thr Lys Ser
                245                 250                 255

Asn Gly Arg Tyr Thr Ala Thr Leu Asp Ala Asp Thr Lys Gln Ser Ser
            260                 265                 270

Leu His Ile Thr Ala Ser Gln Leu Ser Asp Ser Ala Ser Tyr Ile Cys
        275                 280                 285

Val Val Ser Gly Gly Thr Asp Ser Trp Gly Lys Leu Gln Phe Gly Ala
    290                 295                 300

Gly Thr Gln Val Val Val Thr Pro Asp Ile Gln Asn Pro Asp Pro Ala
305             310                 315                 320

Val Tyr Gln Leu Arg Asp Ser Lys Ser Ser Asp Lys Ser Val Cys Leu
                325                 330                 335

Phe Thr Asp Phe Asp Ser Gln Thr Asn Val Ser Gln Ser Lys Asp Ser
            340                 345                 350

Asp Val Tyr Ile Thr Asp Lys Thr Val Leu Asp Met Arg Ser Met Asp
        355                 360                 365

Phe Lys Ser Asn Ser Ala Val Ala Trp Ser Asn Lys Ser Asp Phe Ala
    370                 375                 380

Cys Ala Asn Ala Phe Asn Asn Ser Ile Ile Pro Glu Asp Thr Phe Phe
385             390                 395                 400

Pro Ser Pro Glu Ser Ser Cys Asp Val Lys Leu Val Glu Lys Ser Phe
                405                 410                 415

Glu Thr Asp Thr Asn Leu Asn Phe Gln Asn Leu Ser Val Ile Gly Phe
            420                 425                 430

Arg Ile Leu Leu Leu Lys Val Ala Gly Phe Asn Leu Leu Met Thr Leu
        435                 440                 445

Arg Leu Trp Ser Ser Gly Ser Arg Ala Lys Arg Ser Gly Ser Gly Ala
    450                 455                 460

Thr Asn Phe Ser Leu Leu Lys Gln Ala Gly Asp Val Glu Glu Asn Pro
465             470                 475                 480

Gly Pro Arg Met Ala Ser Leu Leu Phe Phe Cys Gly Ala Phe Tyr Leu
                485                 490                 495

Leu Gly Thr Gly Ser Met Asp Ala Asp Val Thr Gln Thr Pro Arg Asn
            500                 505                 510

Arg Ile Thr Lys Thr Gly Lys Arg Ile Met Leu Glu Cys Ser Gln Thr
        515                 520                 525
```

```
Lys Gly His Asp Arg Met Tyr Trp Tyr Arg Gln Asp Pro Gly Leu Gly
    530                 535                 540

Leu Arg Leu Ile Tyr Tyr Ser Phe Asp Val Lys Asp Ile Asn Lys Gly
545                 550                 555                 560

Glu Ile Ser Asp Gly Tyr Ser Val Ser Arg Gln Ala Gln Ala Lys Phe
                565                 570                 575

Ser Leu Ser Leu Glu Ser Ala Ile Pro Asn Gln Thr Ala Leu Tyr Phe
            580                 585                 590

Cys Ala Thr Ser Gly Gln Gly Ala Tyr Glu Glu Gln Phe Phe Gly Pro
        595                 600                 605

Gly Thr Arg Leu Thr Val Leu Glu Asp Leu Lys Asn Val Phe Pro Pro
    610                 615                 620

Glu Val Ala Val Phe Glu Pro Ser Glu Ala Glu Ile Ser His Thr Gln
625                 630                 635                 640

Lys Ala Thr Leu Val Cys Leu Ala Thr Gly Phe Tyr Pro Asp His Val
                645                 650                 655

Glu Leu Ser Trp Trp Val Asn Gly Lys Glu Val His Ser Gly Val Ser
            660                 665                 670

Thr Asp Pro Gln Pro Leu Lys Glu Gln Pro Ala Leu Asn Asp Ser Arg
        675                 680                 685

Tyr Cys Leu Ser Ser Arg Leu Arg Val Ser Ala Thr Phe Trp Gln Asn
    690                 695                 700

Pro Arg Asn His Phe Arg Cys Gln Val Gln Phe Tyr Gly Leu Ser Glu
705                 710                 715                 720

Asn Asp Glu Trp Thr Gln Asp Arg Ala Lys Pro Val Thr Gln Ile Val
                725                 730                 735

Ser Ala Glu Ala Trp Gly Arg Ala Asp Cys Gly Phe Thr Ser Glu Ser
            740                 745                 750

Tyr Gln Gln Gly Val Leu Ser Ala Thr Ile Leu Tyr Glu Ile Leu Leu
        755                 760                 765

Gly Lys Ala Thr Leu Tyr Ala Val Leu Val Ser Ala Leu Val Leu Met
    770                 775                 780

Ala Met Val Lys Arg Lys Asp Ser Arg Gly
785                 790

<210> SEQ ID NO 7
<211> LENGTH: 2379
<212> TYPE: DNA
<213> ORGANISM: Artificial Sequence
<220> FEATURE:
<223> OTHER INFORMATION: coding sequence for truncated PDE7A with NY-ESO
      TCR

<400> SEQUENCE: 7
atggaagtgt gctaccagct gcccgtgctg cccctggata gacctgtgcc tcagcatgtg      60
ctgagcagaa gaggcgccat cagcttcagc agcagctccg ccctgttcgg ctgccccaat     120
cctagacagc tgagccagag aagggagcc atctcctacg acagcagcga ccagaccgcc      180
ctgtacatca gaatgctggg cgacgtgcgc gtgcggagca gagccggatt tgagagcgag     240
agaagaggct cccaccccta catcgacttc cggatcttcc acagccagag cgagatcgag     300
gtgtccgtgt ccgcccggaa catcagacgg ctgctgagct ccagagata cctgagaagc      360 agccggttct ccgggggcac cgccgtgtcc aacagcctga catcctgga cgacgactac      420 aacggccagg ccaagcgggc caagagatct ggaagcggag ccctgtgaa gcagaccctg      480 aacttcgatc tgctgaaact ggccggcgac gtggaaagca accctggccc catggaaaca     540
```

```
ctgctgggac tgctgatcct gtggctgcag ctgcagtggg tgtccagcaa gcaggaggtg    600
acccagatcc ctgccgccct gagcgtgccc gagggcgaga acctggtgct gaactgcagc    660
ttcaccgact ccgccatcta caacctgcag tggttccggc aggaccccgg caagggcctg    720
accagcctgc tgctgatcca gagcagccag cgggagcaga ccagcggacg gctgaacgcc    780
agcctggaca gagcagcggc ccggagcacc ctgtacatcg ccgccagcca gcccggcgac    840
agcgccacct acctgtgcgc tgtgcggcct ctgtacggcg gcagctacat ccccaccttc    900
ggcagaggca ccagcctgat cgtgcacccc tacatccaga accccgaccc cgccgtgtac    960
cagctgcggg acagcaagag cagcgacaag tctgtgtgcc tgttcaccga cttcgacagc   1020
cagaccaatg tgagccagag caaggacagc gacgtgtaca tcaccgacaa gaccgtgctg   1080
gacatgcgga gcatggactt caagagcaac agcgccgtgg cctggagcaa caagagcgac   1140
ttcgcctgcg ccaacgcctt caacaacagc attatccccg aggacacctt cttccccagc   1200
cccgagagca gctgcgacgt gaaactggtg gagaagagct cgagaccga caccaacctg   1260 aacttccaga acctgagcgt gatcggcttc agaatcctgc tgctgaaggt ggccggattc   1320
aacctgctga tgaccctgcg gctgtggagc agcggctccc gggccaagag aagcggatcc   1380
ggcgccacca acttcagcct gctgaagcag gccggagacg tggaagaaaa ccctggccct   1440
aggatgagca tcggcctgct gtgctgcgcc gccctgagcc tgctgtgggc aggacccgtg   1500
aacgccggag tgacccagac ccccaagttc caggtgctga aaaccggcca gagcatgacc   1560
ctgcagtgcg cccaggacat gaaccacgag tacatgagct ggtatcggca ggaccccggc   1620
atgggcctgc ggctgatcca ctactctgtg ggagccggaa tcaccgacca gggcgaggtg   1680
cccaacggct acaatgtgag ccggagcacc accgaggact cccccctgcg gctgctgagc   1740 gctgcccca gccagaccag cgtgtacttc tgcgccagca gctatgtggg caacaccggc   1800
gagctgttct cggcgaggg ctccaggctg accgtgctgg aggacctgaa gaacgtgttc   1860 cccccgagg tggccgtgtt cgagcccagc gaggccgaga tcagccacac ccagaaggcc   1920
acactggtgt gtctggccac cggcttctac cccgaccacg tggagctgtc ctggtgggtg   1980
aacggcaagg aggtgcacag cggcgtgtct accgaccccc agcccctgaa ggagcagccc   2040
gccctgaacg acagccggta ctgcctgtcc tccagactga gagtgagcgc caccttctgg   2100 cagaacccc ggaaccactt ccggtgccag gtgcagttct acggcctgag cgagaacgac   2160
gagtggaccc aggaccgggc caagcccgtg acccagattg tgagcgccga ggcctggggc   2220
agggccgact gcggcttcac cagcgagagc taccagcagg gcgtgctgag cgccaccatc   2280
ctgtacgaga tcctgctggg caaggccacc ctgtacgccg tgctggtgtc tgccctggtg   2340
ctgatggcta tggtgaagcg gaaggacagc cggggctaa                          2379
```

<210> SEQ ID NO 8
<211> LENGTH: 792
<212> TYPE: PRT
<213> ORGANISM: Artificial Sequence
<220> FEATURE:
<223> OTHER INFORMATION: amino acid sequence for truncated PDE7A with
      NY-ESO TCR

<400> SEQUENCE: 8

Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser Ser
            20                  25                  30

-continued

Ser Ala Leu Phe Gly Cys Pro Asn Pro Arg Gln Leu Ser Gln Arg Arg
         35                  40                  45

Gly Ala Ile Ser Tyr Asp Ser Asp Gln Thr Ala Leu Tyr Ile Arg
 50                  55                  60

Met Leu Gly Asp Val Arg Val Arg Ser Arg Ala Gly Phe Glu Ser Glu
 65                  70                  75                  80

Arg Arg Gly Ser His Pro Tyr Ile Asp Phe Arg Ile Phe His Ser Gln
             85                  90                  95

Ser Glu Ile Glu Val Ser Val Ser Ala Arg Asn Ile Arg Arg Leu Leu
                100                 105                 110

Ser Phe Gln Arg Tyr Leu Arg Ser Ser Arg Phe Arg Gly Thr Ala
        115                 120                 125

Val Ser Asn Ser Leu Asn Ile Leu Asp Asp Tyr Asn Gly Gln Ala
130                 135                 140

Lys Arg Ala Lys Arg Ser Gly Ser Gly Ala Pro Val Lys Gln Thr Leu
145                 150                 155                 160

Asn Phe Asp Leu Leu Lys Leu Ala Gly Asp Val Glu Ser Asn Pro Gly
                165                 170                 175

Pro Met Glu Thr Leu Leu Gly Leu Leu Ile Leu Trp Leu Gln Leu Gln
            180                 185                 190

Trp Val Ser Ser Lys Gln Glu Val Thr Gln Ile Pro Ala Ala Leu Ser
        195                 200                 205

Val Pro Glu Gly Glu Asn Leu Val Leu Asn Cys Ser Phe Thr Asp Ser
210                 215                 220

Ala Ile Tyr Asn Leu Gln Trp Phe Arg Gln Asp Pro Gly Lys Gly Leu
225                 230                 235                 240

Thr Ser Leu Leu Leu Ile Gln Ser Ser Gln Arg Glu Gln Thr Ser Gly
                245                 250                 255

Arg Leu Asn Ala Ser Leu Asp Lys Ser Ser Gly Arg Ser Thr Leu Tyr
            260                 265                 270

Ile Ala Ala Ser Gln Pro Gly Asp Ser Ala Thr Tyr Leu Cys Ala Val
        275                 280                 285

Arg Pro Leu Tyr Gly Gly Ser Tyr Ile Pro Thr Phe Gly Arg Gly Thr
290                 295                 300

Ser Leu Ile Val His Pro Tyr Ile Gln Asn Pro Asp Pro Ala Val Tyr
305                 310                 315                 320

Gln Leu Arg Asp Ser Lys Ser Ser Asp Lys Ser Val Cys Leu Phe Thr
                325                 330                 335

Asp Phe Asp Ser Gln Thr Asn Val Ser Gln Ser Lys Asp Ser Asp Val
            340                 345                 350

Tyr Ile Thr Asp Lys Thr Val Leu Asp Met Arg Ser Met Asp Phe Lys
        355                 360                 365

Ser Asn Ser Ala Val Ala Trp Ser Asn Lys Ser Asp Phe Ala Cys Ala
370                 375                 380

Asn Ala Phe Asn Asn Ser Ile Ile Pro Glu Asp Thr Phe Phe Pro Ser
385                 390                 395                 400

Pro Glu Ser Ser Cys Asp Val Lys Leu Val Glu Lys Ser Phe Glu Thr
                405                 410                 415

Asp Thr Asn Leu Asn Phe Gln Asn Leu Ser Val Ile Gly Phe Arg Ile
            420                 425                 430

Leu Leu Leu Lys Val Ala Gly Phe Asn Leu Leu Met Thr Leu Arg Leu
        435                 440                 445

Trp Ser Ser Gly Ser Arg Ala Lys Arg Ser Gly Ser Gly Ala Thr Asn
450                 455                 460

Phe Ser Leu Leu Lys Gln Ala Gly Asp Val Glu Glu Asn Pro Gly Pro
465                 470                 475                 480

Arg Met Ser Ile Gly Leu Leu Cys Cys Ala Ala Leu Ser Leu Leu Trp
                485                 490                 495

Ala Gly Pro Val Asn Ala Gly Val Thr Gln Thr Pro Lys Phe Gln Val
                500                 505                 510

Leu Lys Thr Gly Gln Ser Met Thr Leu Gln Cys Ala Gln Asp Met Asn
                515                 520                 525

His Glu Tyr Met Ser Trp Tyr Arg Gln Asp Pro Gly Met Gly Leu Arg
530                 535                 540

Leu Ile His Tyr Ser Val Gly Ala Gly Ile Thr Asp Gln Gly Glu Val
545                 550                 555                 560

Pro Asn Gly Tyr Asn Val Ser Arg Ser Thr Thr Glu Asp Phe Pro Leu
                565                 570                 575

Arg Leu Leu Ser Ala Ala Pro Ser Gln Thr Ser Val Tyr Phe Cys Ala
                580                 585                 590

Ser Ser Tyr Val Gly Asn Thr Gly Glu Leu Phe Phe Gly Glu Gly Ser
                595                 600                 605

Arg Leu Thr Val Leu Glu Asp Leu Lys Asn Val Phe Pro Pro Glu Val
                610                 615                 620

Ala Val Phe Glu Pro Ser Glu Ala Glu Ile Ser His Thr Gln Lys Ala
625                 630                 635                 640

Thr Leu Val Cys Leu Ala Thr Gly Phe Tyr Pro Asp His Val Glu Leu
                645                 650                 655

Ser Trp Trp Val Asn Gly Lys Glu Val His Ser Gly Val Ser Thr Asp
                660                 665                 670

Pro Gln Pro Leu Lys Glu Gln Pro Ala Leu Asn Asp Ser Arg Tyr Cys
                675                 680                 685

Leu Ser Ser Arg Leu Arg Val Ser Ala Thr Phe Trp Gln Asn Pro Arg
690                 695                 700

Asn His Phe Arg Cys Gln Val Gln Phe Tyr Gly Leu Ser Glu Asn Asp
705                 710                 715                 720

Glu Trp Thr Gln Asp Arg Ala Lys Pro Val Thr Gln Ile Val Ser Ala
                725                 730                 735

Glu Ala Trp Gly Arg Ala Asp Cys Gly Phe Thr Ser Glu Ser Tyr Gln
                740                 745                 750

Gln Gly Val Leu Ser Ala Thr Ile Leu Tyr Glu Ile Leu Leu Gly Lys
                755                 760                 765

Ala Thr Leu Tyr Ala Val Leu Val Ser Ala Leu Val Leu Met Ala Met
770                 775                 780

Val Lys Arg Lys Asp Ser Arg Gly
785                 790

<210> SEQ ID NO 9
<211> LENGTH: 18
<212> TYPE: PRT
<213> ORGANISM: Artificial Sequence
<220> FEATURE:
<223> OTHER INFORMATION: repeat amino acid sequence
<220> FEATURE:
<221> NAME/KEY: VARIANT
<222> LOCATION: (2)..(2)
<223> OTHER INFORMATION: Xaa is Val or Asn
<220> FEATURE:
<221> NAME/KEY: VARIANT

```
<222> LOCATION: (4)..(4)
<223> OTHER INFORMATION: Xaa is Gln or Arg
<220> FEATURE:
<221> NAME/KEY: VARIANT
<222> LOCATION: (5)..(5)
<223> OTHER INFORMATION: Xaa is His or Gln
<220> FEATURE:
<221> NAME/KEY: VARIANT
<222> LOCATION: (6)..(6)
<223> OTHER INFORMATION: Xaa is Val or Leu
<220> FEATURE:
<221> NAME/KEY: VARIANT
<222> LOCATION: (7)..(7)
<223> OTHER INFORMATION: Xaa is Leu or Ser
<220> FEATURE:
<221> NAME/KEY: VARIANT
<222> LOCATION: (8)..(8)
<223> OTHER INFORMATION: Xaa is Ser or Gln
<220> FEATURE:
<221> NAME/KEY: VARIANT
<222> LOCATION: (15)..(15)
<223> OTHER INFORMATION: Xaa is Phe or Tyr
<220> FEATURE:
<221> NAME/KEY: VARIANT
<222> LOCATION: (16)..(16)
<223> OTHER INFORMATION: Xaa is Ser or Ser

<400> SEQUENCE: 9

Pro Xaa Pro Xaa Xaa Xaa Xaa Xaa Arg Arg Gly Ala Ile Ser Xaa Xaa
1               5                   10                  15

Ser Ser

<210> SEQ ID NO 10
<211> LENGTH: 10
<212> TYPE: PRT
<213> ORGANISM: Artificial Sequence
<220> FEATURE:
<223> OTHER INFORMATION: amino acid tag

<400> SEQUENCE: 10

Met Arg Gly Ser His His His His His His
1               5                   10

<210> SEQ ID NO 11
<211> LENGTH: 8
<212> TYPE: PRT
<213> ORGANISM: Artificial Sequence
<220> FEATURE:
<223> OTHER INFORMATION: amino acid tag

<400> SEQUENCE: 11

Asp Tyr Lys Asp Asp Asp Asp Lys
1               5

<210> SEQ ID NO 12
<211> LENGTH: 15
<212> TYPE: PRT
<213> ORGANISM: Artificial Sequence
<220> FEATURE:
<223> OTHER INFORMATION: amino acid tag

<400> SEQUENCE: 12

Lys Glu Thr Ala Ala Ala Lys Phe Glu Arg Gln His Met Asp Ser
1               5                   10                  15

<210> SEQ ID NO 13
<211> LENGTH: 5
<212> TYPE: PRT
<213> ORGANISM: Artificial Sequence
<220> FEATURE:
```

<223> OTHER INFORMATION: amino acid tag

<400> SEQUENCE: 13

Arg Arg Arg Arg Arg
1               5

<210> SEQ ID NO 14
<211> LENGTH: 6
<212> TYPE: PRT
<213> ORGANISM: Artificial Sequence
<220> FEATURE:
<223> OTHER INFORMATION: amino acid tag

<400> SEQUENCE: 14

Arg Arg Arg Arg Arg Arg
1               5

<210> SEQ ID NO 15
<211> LENGTH: 4
<212> TYPE: PRT
<213> ORGANISM: Artificial Sequence
<220> FEATURE:
<223> OTHER INFORMATION: amino acid tag

<400> SEQUENCE: 15

His His His His
1

<210> SEQ ID NO 16
<211> LENGTH: 5
<212> TYPE: PRT
<213> ORGANISM: Artificial Sequence
<220> FEATURE:
<223> OTHER INFORMATION: amino acid tag

<400> SEQUENCE: 16

His His His His His
1               5

<210> SEQ ID NO 17
<211> LENGTH: 6
<212> TYPE: PRT
<213> ORGANISM: Artificial Sequence
<220> FEATURE:
<223> OTHER INFORMATION: amino acid tag

<400> SEQUENCE: 17

His His His His His His
1               5

<210> SEQ ID NO 18
<211> LENGTH: 7
<212> TYPE: PRT
<213> ORGANISM: Artificial Sequence
<220> FEATURE:
<223> OTHER INFORMATION: amino acid tag

<400> SEQUENCE: 18

His His His His His His His
1               5

<210> SEQ ID NO 19
<211> LENGTH: 8
<212> TYPE: PRT
<213> ORGANISM: Artificial Sequence
<220> FEATURE:
<223> OTHER INFORMATION: amino acid tag

```
<400> SEQUENCE: 19

His His His His His His His His
1               5

<210> SEQ ID NO 20
<211> LENGTH: 9
<212> TYPE: PRT
<213> ORGANISM: Artificial Sequence
<220> FEATURE:
<223> OTHER INFORMATION: amino acid tag

<400> SEQUENCE: 20

His His His His His His His His His
1               5

<210> SEQ ID NO 21
<211> LENGTH: 10
<212> TYPE: PRT
<213> ORGANISM: Artificial Sequence
<220> FEATURE:
<223> OTHER INFORMATION: amino acid tag

<400> SEQUENCE: 21

His His His His His His His His His His
1               5                   10

<210> SEQ ID NO 22
<211> LENGTH: 4
<212> TYPE: PRT
<213> ORGANISM: Artificial Sequence
<220> FEATURE:
<223> OTHER INFORMATION: amino acid tag

<400> SEQUENCE: 22

Cys Cys Cys Cys
1

<210> SEQ ID NO 23
<211> LENGTH: 11
<212> TYPE: PRT
<213> ORGANISM: Artificial Sequence
<220> FEATURE:
<223> OTHER INFORMATION: amino acid tag

<400> SEQUENCE: 23

Phe Phe Phe Phe Phe Phe Phe Phe Phe Phe Phe
1               5                   10

<210> SEQ ID NO 24
<211> LENGTH: 5
<212> TYPE: PRT
<213> ORGANISM: Artificial Sequence
<220> FEATURE:
<223> OTHER INFORMATION: amino acid tag

<400> SEQUENCE: 24

Asp Asp Asp Asp Asp
1               5

<210> SEQ ID NO 25
<211> LENGTH: 6
<212> TYPE: PRT
<213> ORGANISM: Artificial Sequence
<220> FEATURE:
<223> OTHER INFORMATION: amino acid tag
```

```
<400> SEQUENCE: 25

Asp Asp Asp Asp Asp Asp
1               5

<210> SEQ ID NO 26
<211> LENGTH: 7
<212> TYPE: PRT
<213> ORGANISM: Artificial Sequence
<220> FEATURE:
<223> OTHER INFORMATION: amino acid tag

<400> SEQUENCE: 26

Asp Asp Asp Asp Asp Asp Asp
1               5

<210> SEQ ID NO 27
<211> LENGTH: 8
<212> TYPE: PRT
<213> ORGANISM: Artificial Sequence
<220> FEATURE:
<223> OTHER INFORMATION: amino acid tag

<400> SEQUENCE: 27

Asp Asp Asp Asp Asp Asp Asp Asp
1               5

<210> SEQ ID NO 28
<211> LENGTH: 9
<212> TYPE: PRT
<213> ORGANISM: Artificial Sequence
<220> FEATURE:
<223> OTHER INFORMATION: amino acid tag

<400> SEQUENCE: 28

Asp Asp Asp Asp Asp Asp Asp Asp Asp
1               5

<210> SEQ ID NO 29
<211> LENGTH: 10
<212> TYPE: PRT
<213> ORGANISM: Artificial Sequence
<220> FEATURE:
<223> OTHER INFORMATION: amino acid tag

<400> SEQUENCE: 29

Asp Asp Asp Asp Asp Asp Asp Asp Asp Asp
1               5                   10

<210> SEQ ID NO 30
<211> LENGTH: 11
<212> TYPE: PRT
<213> ORGANISM: Artificial Sequence
<220> FEATURE:
<223> OTHER INFORMATION: amino acid tag

<400> SEQUENCE: 30

Asp Asp Asp Asp Asp Asp Asp Asp Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: amino acid tag

<400> SEQUENCE: 31
```

```
Asp Asp Asp Asp Asp Asp Asp Asp Asp Asp Asp
1               5                   10

<210> SEQ ID NO 32
<211> LENGTH: 13
<212> TYPE: PRT
<213> ORGANISM: Artificial Sequence
<220> FEATURE:
<223> OTHER INFORMATION: amino acid tag

<400> SEQUENCE: 32

Asp Asp Asp Asp Asp Asp Asp Asp Asp Asp Asp Asp Asp
1               5                   10

<210> SEQ ID NO 33
<211> LENGTH: 14
<212> TYPE: PRT
<213> ORGANISM: Artificial Sequence
<220> FEATURE:
<223> OTHER INFORMATION: amino acid tag

<400> SEQUENCE: 33

Asp Asp Asp Asp Asp Asp Asp Asp Asp Asp Asp Asp Asp Asp
1               5                   10

<210> SEQ ID NO 34
<211> LENGTH: 15
<212> TYPE: PRT
<213> ORGANISM: Artificial Sequence
<220> FEATURE:
<223> OTHER INFORMATION: amino acid tag

<400> SEQUENCE: 34

Asp Asp Asp Asp Asp Asp Asp Asp Asp Asp Asp Asp Asp Asp Asp
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: amino acid tag

<400> SEQUENCE: 35

Asp Asp Asp Asp Asp Asp Asp Asp Asp Asp Asp Asp Asp Asp Asp Asp
1               5                   10                  15

<210> SEQ ID NO 36
<211> LENGTH: 10
<212> TYPE: PRT
<213> ORGANISM: Artificial Sequence
<220> FEATURE:
<223> OTHER INFORMATION: amino acid tag

<400> SEQUENCE: 36

Glu Gln Lys Leu Ile Ser Glu Glu Asp Leu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: amino acid tag

<400> SEQUENCE: 37
```

```
Met Lys Ala Glu Phe Arg Arg Gln Glu Ser Asp Arg
1               5                   10
```

```
<210> SEQ ID NO 38
<211> LENGTH: 12
<212> TYPE: PRT
<213> ORGANISM: Artificial Sequence
<220> FEATURE:
<223> OTHER INFORMATION: amino acid tag

<400> SEQUENCE: 38

Met Arg Asp Ala Leu Asp Arg Leu Asp Arg Leu Ala
1               5                   10
```

```
<210> SEQ ID NO 39
<211> LENGTH: 9
<212> TYPE: PRT
<213> ORGANISM: Artificial Sequence
<220> FEATURE:
<223> OTHER INFORMATION: amino acid tag

<400> SEQUENCE: 39

Tyr Pro Tyr Asp Val Pro Asp Tyr Ala
1               5
```

```
<210> SEQ ID NO 40
<211> LENGTH: 8
<212> TYPE: PRT
<213> ORGANISM: Artificial Sequence
<220> FEATURE:
<223> OTHER INFORMATION: amino acid tag

<400> SEQUENCE: 40

Trp Ser His Pro Gln Phe Glu Lys
1               5
```